(12) United States Patent
Borody et al.

(10) Patent No.: US 10,092,573 B2
(45) Date of Patent: Oct. 9, 2018

(54) GASTRIC AND COLONIC FORMULATIONS AND METHODS FOR MAKING AND USING THEM

(75) Inventors: Thomas Julius Borody, Five Dock (AU); Sanjay Ramrakha, Haberfield (AU); John Saxon, Bellevue Hill (AU); Antony Wettstein, Killara (AU)

(73) Assignee: Salix Pharmaceuticals, Inc., Raleigh, NC (US)

( * ) Notice: Subject to any disclaimer, the term of this patent is extended or adjusted under 35 U.S.C. 154(b) by 5 days.

(21) Appl. No.: 13/993,294

(22) PCT Filed: Dec. 13, 2011

(86) PCT No.: PCT/AU2011/001609
§ 371 (c)(1),
(2), (4) Date: Jul. 8, 2013

(87) PCT Pub. No.: WO2012/079118
PCT Pub. Date: Jun. 21, 2012

(65) Prior Publication Data
US 2013/0296314 A1    Nov. 7, 2013

Related U.S. Application Data

(60) Provisional application No. 61/422,567, filed on Dec. 13, 2010.

(51) Int. Cl.
| | |
|---|---|
| A61K 31/538 | (2006.01) |
| A61K 31/047 | (2006.01) |
| A61K 31/4402 | (2006.01) |
| A61K 31/4412 | (2006.01) |
| A61K 45/06 | (2006.01) |

(52) U.S. Cl.
CPC .......... *A61K 31/538* (2013.01); *A61K 31/047* (2013.01); *A61K 31/4402* (2013.01); *A61K 31/4412* (2013.01); *A61K 45/06* (2013.01)

(58) Field of Classification Search
CPC .............. A61K 31/047; A61K 31/4402; A61K 31/4412; A61K 45/06
USPC .................................................... 514/230.5
See application file for complete search history.

(56) References Cited

U.S. PATENT DOCUMENTS

| | | | |
|---|---|---|---|
| 4,186,025 A | 1/1980 | Kang et al. | |
| 4,452,779 A | 6/1984 | Cockerill | |
| 4,766,004 A | 8/1988 | Moskowitz | |
| 4,975,286 A | 12/1990 | Hechter | |
| 5,173,296 A | 12/1992 | Andre et al. | |
| 5,196,205 A | 3/1993 | Borody | |
| 5,213,807 A | 5/1993 | Chemburkar et al. | |
| 5,232,699 A | 8/1993 | Colliopoulos | |
| 5,274,001 A | 12/1993 | Borody | |
| 5,443,826 A | 8/1995 | Borody | |
| 5,476,669 A | 12/1995 | Borody | |
| 5,519,014 A | 5/1996 | Borody | |
| 5,631,022 A | 5/1997 | Mandel et al. | |
| 5,858,403 A | 1/1999 | Borody et al. | |
| 6,087,386 A | 7/2000 | Chen et al. | |
| 6,103,268 A | 8/2000 | Borody et al. | |
| 6,121,250 A | 9/2000 | Nishiyama et al. | |
| 6,132,767 A | 10/2000 | Borody et al. | |
| 6,162,464 A | 12/2000 | Jacob et al. | |
| 6,245,740 B1 | 6/2001 | Goldenberg et al. | |
| 6,277,836 B1 | 8/2001 | Borody | |
| 6,284,274 B1 | 9/2001 | Merrill et al. | |
| 6,303,662 B1 * | 10/2001 | Nagahama et al. | .......... 424/522 |
| 6,426,338 B1 | 7/2002 | Borody | |
| 6,475,510 B1 | 11/2002 | Venkatesh et al. | |
| 6,475,518 B1 | 11/2002 | Baumgart et al. | |
| 6,489,317 B1 | 12/2002 | Borody | |
| 6,514,531 B1 | 2/2003 | Alaux et al. | |
| 6,551,632 B2 | 4/2003 | Borody | |

(Continued)

FOREIGN PATENT DOCUMENTS

| | | |
|---|---|---|
| AU | 771576 B2 | 3/2004 |
| CA | 2189418 A1 | 5/1997 |

(Continued)

OTHER PUBLICATIONS

Rider et al (Current Therapeutic Research. vol. 13, No. 6, Jun. 1971).*
Oku et al (Nutrition Research, vol. 16. No. 4, pp. 577-589, 1996).*
Kienzle-Horn et al (Current Medical Research and Opinions, vol. 23, No. 4, 2007, 691-699).*
Stahl et al. (Handbook of Pharmaceutical Salts: Properties, Selection and Use. 2008).*
Arrigoni et al (British Journal of Nutrition (2005), 94, 643-646).*
Noda et al., "Metabolism and Disposition of Erythritol after Oral Administration to Rats", JN The Journal of Nutrition, 1992, pp. 1266-1272.
Umehara, International Search Report, PCT/AU2011/001609, dated Jan. 17, 2012, Australian Patent Office.

(Continued)

*Primary Examiner* — Angela C Brown-Pettigrew
(74) *Attorney, Agent, or Firm* — McCarter & English, LLP; Jonathan M. Sparks

(57) ABSTRACT

In alternative embodiments, the invention provides compositions, e.g., formulations, used for gastric, gastrointestinal and/or colonic treatments or lavage, e.g., orthostatic lavage, e.g., for inducing the purgation (e.g., cleansing) of a gastrointestinal (GI) tract, including a colon; and methods for making and using them. In alternative embodiments, compositions and methods of the invention are used for the amelioration, treatment and/or prevention of constipation, for the treatment of abdominal pain, particularly non-specific abdominal pain, and diarrhea, including diarrhea caused by a drug side effect, a psychological condition, a disease or a condition such as Crohn's Disease, a poison, a toxin or an infection, e.g., a toxin-mediated traveler's diarrhea. In alternative embodiments, the invention provides pharmaceuticals and products (articles) of manufacture for delivering these compositions and formulations to an individual, e.g., a human or an animal.

51 Claims, No Drawings

(56) References Cited

U.S. PATENT DOCUMENTS

| | | |
|---|---|---|
| 6,645,530 B1 | 11/2003 | Borody |
| 6,774,111 B1 | 8/2004 | Wolf et al. |
| 6,858,403 B2 | 2/2005 | Han et al. |
| 6,926,907 B2 | 8/2005 | Plachetka |
| 6,979,674 B1 | 12/2005 | Goldenberg et al. |
| 7,763,276 B1 | 7/2010 | Shodai et al. |
| 7,799,341 B2 | 9/2010 | Porzio et al. |
| 7,815,956 B2 | 10/2010 | Lee et al. |
| 7,846,475 B2 | 12/2010 | Shiraishi et al. |
| 7,993,682 B2 | 8/2011 | Borody et al. |
| 8,679,549 B2 | 3/2014 | Borody et al. |
| 2002/0035075 A1 | 3/2002 | Borody |
| 2002/0071872 A1 | 6/2002 | McNally et al. |
| 2003/0092724 A1 | 5/2003 | Kao et al. |
| 2003/0175336 A1 | 9/2003 | Luber et al. |
| 2003/0180260 A1 | 9/2003 | Clancy et al. |
| 2003/0202957 A1 | 10/2003 | Cleveland |
| 2004/0009961 A1 | 1/2004 | Borody |
| 2004/0028689 A1 | 2/2004 | Borody |
| 2004/0038329 A1 | 2/2004 | Clancy et al. |
| 2004/0259899 A1* | 12/2004 | Sanghvi et al. ............... 514/282 |
| 2006/0275223 A1 | 12/2006 | Burr |
| 2007/0281905 A1* | 12/2007 | Gripp et al. .................... 514/63 |
| 2008/0299197 A1 | 12/2008 | Toneguzzo et al. |
| 2009/0155363 A1 | 6/2009 | Maibach |
| 2009/0258090 A1 | 10/2009 | Cleveland |
| 2010/0178349 A1 | 7/2010 | Kolter et al. |
| 2010/0178413 A1 | 7/2010 | Gorris |
| 2010/0184785 A1 | 7/2010 | Kolter et al. |
| 2010/0222311 A1 | 9/2010 | Thommes et al. |
| 2010/0226866 A1 | 9/2010 | Yamashiro et al. |
| 2010/0233278 A1 | 9/2010 | Ookawa et al. |
| 2010/0239667 A1 | 9/2010 | Hemmingsen et al. |
| 2010/0247665 A1 | 9/2010 | Takahashi |
| 2010/0255307 A1 | 10/2010 | Gonze et al. |
| 2010/0278930 A1 | 11/2010 | Okumura et al. |
| 2010/0285164 A1 | 11/2010 | Schaible et al. |
| 2010/0289164 A1 | 11/2010 | Porzio et al. |
| 2010/0297031 A1 | 11/2010 | beda Perez et al. |
| 2011/0218216 A1 | 9/2011 | Vivek et al. |
| 2011/0223252 A1 | 9/2011 | Borody et al. |
| 2012/0064133 A1 | 3/2012 | Chauhan et al. |
| 2012/0183612 A1 | 7/2012 | Brogmann et al. |

FOREIGN PATENT DOCUMENTS

| | | |
|---|---|---|
| CA | 2335713 A1 | 11/2001 |
| CN | 1288730 A | 3/2001 |
| EP | 0397689 A1 | 11/1990 |
| EP | 0439453 A4 | 2/1991 |
| EP | 0433299 A1 | 6/1991 |
| EP | 0554291 A1 | 8/1993 |
| EP | 0771562 A2 | 5/1997 |
| JP | S58-222020 A | 12/1983 |
| JP | 5306221 A | 11/1993 |
| JP | 07242539 A | 9/1995 |
| JP | H08-310960 A | 11/1996 |
| JP | 2001114668 | 4/2001 |
| JP | 2004-292356 A | 10/2004 |
| JP | 2008-501683 A | 1/2008 |
| JP | 2008-115085 A | 5/2008 |
| NZ | 333493 A | 6/2000 |
| RU | 2098100 C1 | 10/1997 |
| WO | 8501441 | 4/1985 |
| WO | 8605981 A1 | 10/1986 |
| WO | 8903219 A1 | 4/1989 |
| WO | 8905659 A1 | 6/1989 |
| WO | 9001335 | 2/1990 |
| WO | 9206690 A1 | 4/1992 |
| WO | 9602236 A1 | 2/1996 |
| WO | 9611014 | 4/1996 |
| WO | 9843654 | 10/1998 |
| WO | 9843667 A1 | 10/1998 |
| WO | 9850043 A1 | 11/1998 |
| WO | 9956749 A1 | 11/1999 |
| WO | 0001378 A1 | 1/2000 |
| WO | 0167895 A1 | 9/2001 |
| WO | 0180852 A1 | 11/2001 |
| WO | 0197821 A1 | 12/2001 |
| WO | 0203065 | 1/2002 |
| WO | 0207741 | 1/2002 |
| WO | 2002071872 A2 | 9/2002 |
| WO | 03061767 A1 | 7/2003 |
| WO | 03074061 A1 | 9/2003 |
| WO | 2004070043 A1 | 8/2004 |
| WO | 2004/100857 A2 | 11/2004 |
| WO | 2005051361 A1 | 6/2005 |
| WO | 2005/120501 A1 | 12/2005 |
| WO | 2006118370 A1 | 11/2006 |
| WO | 2007057924 A1 | 5/2007 |
| WO | 2007/088489 A2 | 8/2007 |
| WO | 2008021394 A2 | 2/2008 |
| WO | 2008027442 A2 | 3/2008 |
| WO | 2008141368 A1 | 11/2008 |
| WO | 2012079118 A1 | 6/2012 |
| WO | 2013059881 A1 | 5/2013 |
| WO | 2014016671 A2 | 1/2014 |
| WO | 2014032108 A1 | 3/2014 |

OTHER PUBLICATIONS

U.S. Appl. No. 13/593,092, filed Jun. 29, 2012.
U.S. Appl. No. 10/506,728, field Mar. 4, 2003.
U.S. Appl. No. 14/353,744, Pending, filed Oct. 27, 2012.
Alternative Sweetners (O'Brien Nabors, ed. (2001), p. 3).
Andrews PJ, et al., "'Putting back the bugs': bacterial treatment relieves chronic constipation and symptoms of irritable bowel syndrome", Med J Aust. Nov. 1;159(9):633-4 (1993).
Borody TJ, "'Flora Power'—fecal bacteria cure chronic C. difficile diarrhea", Am J Gastroenterol. Nov. ;95(11):3028-9 (2000).
Borody TJ, "Helicobacter pylori eradication failure—'salvage' therapies needed", Ital J Gastroenterol Hepatol. Aug. ;30(4):375-7 (1998).
Borody TJ, Andrews P, Jankiewicz E, Ferch N, Carroll M, "Apparent reversal of early gastric mucosal atrophy after triple therapy for Helicobacter pylori", Am J Gastroenterol. Aug. ; 88(8):1266-68 (1993).
Borody TJ, Ashman O., "Lactoferrin: milking ulcers?", Dig Liver Dis. Oct. ;35(10):691-3. (2003).
Borody TJ, Brandt S, Andrews P, Ferch N, Jankiewicz E, Hyland L, "Use of high efficacy, lower dose triple therapy to reduce side effects of eradicating Helicobacter pylori", Am J Gastroenterol. Jan. ;89(1):33-8 (1994).
Borody TJ, George L, Andrews P, Brandi S, Noonan S, Cole P, Hyland L, Morgan A, Maysey J, Moore-Jones D, "Bowel-flora alteration: a potential cure for inflammatory bowel disease and irritable bowel syndrome?", Med J Aust. May 15;150(10):604 (1989).
Borody TJ, George LL, Brandl S, Andrews P, Lenne J, Moore-Jones D, Devine M, Walton M, "Helicobacter pylori eradication with doxycycline-metronidazole-bismuth subcitrate triple therapy", Scand J Gastroenterol. Apr.;27(4):281-4 (1992).
Borody TJ, Warren EF, Leis S, Surace R, Ashman O, "Treatment of ulcerative colitis using fecal bacteriotherapy", J Clin Gastroenterol. Jul. ;17(1):42-7 (2003).
Borody TJ, Warren EF, Leis SM, Surace R, Ashman O, Siarakas S., "Bacteriotherapy using fecal flora: toying with human motions", J Clin Gastroenterol Jul.;38(6):475-83 (2004).
Borody, et al., "Eradication therapies for Helicobacter pylori", J Gastroenterol. 33 Supp 10:53-6 (1998).
Borody, Thomas J., Giaconda Limited Newsletter, Issue 2, Dec. 2006.
Borody, Thomas J., News Release Giaconda Limited, Giaconda announces positive phase II data for PICOCONDA. Presented at Australian Gastroenterology Week, Oct. 10, 2006.
Burger, S.A., et al., "A Mannitol-Bisacodyl Regimen for Radiological Visualization of the Colon," SA Medical Journal, Jul. 14, 1979. Retrieved from the Internet: http://archive.samj.org.za/1979%20VOL%20LVI%20Jul-Dec/Articles/01%20July/2.9%20A%

(56) References Cited

OTHER PUBLICATIONS

20MANNITOL-BISACODYL%20REGIMEN%20FOR%20RADIO-LOGICAL%20VISUALIZATION%20OF%20THE%20COLON,%20S.A.Burger,%20D.Spies.pdf.
de Boer WA, Borody TJ, "Treatment failures and secondary resistance to antibiotics. A growing concern in Helicobacter pylori therapy", Dig Liver Dis. Nov.;32(8):673-5 (2000).
Derwent Abstract Accession No. 93-408836, JP 05306221 A (Horii Yakunhin Kogyo KK) "Intestinal rinse soln. contains magnesium citrate, sodium chloride, potassium hydroxide and sugar", Nov. 19, 1993 Abstract Only.
Derwent Abstract Accession No. 98-375395, RU 2098100 C1 (Maksimova et al.), "Intestinal rinse soln. contains magnesium citrate, sodium chloride, potassium hydroxide and sugar" Dec. 10, 1997 Abstract Only.
Duthie, J. "Do you really know what you are drinking?", Nutri Dat 18(1): 5-8 (2007).
Dye, D., "The inadequacy of the usual determinative tests for the identification of *Xanthomonas* SPP," New Zealand Journal of Science5(4):393-416 (1962).
Extended European Search Report, Application No. EP11848334, dated Mar. 14, 2014.
International Preliminary Report on Patentability, International Application No. PCT/AU2011/001609, dated Dec. 13, 2011.
International Preliminary Report on Patentability, International Application No. PCT/AU2012/001315, dated Oct. 27, 2012.
International Search Report, International Application No. PCT/AU03/00257, dated Apr. 24, 2003.
International Search Report, International Application No. PCT/AU2011/001609, dated Jan. 17, 2012.
International Search Report, International Application No. PCT/AU2012/001315, dated Oct. 27, 2012.
International Search Report, International Application No. PCT/AU2013/000973, dated Aug. 29, 2013.
JP 07242539, Fukahori, A. et al., "Compositions having laxative effect, used in treatment of constipation comprise organic acid, sugar alcohol, and optional calcium salts", 1995, Derwent Abstract, pp. 1-7.
Kawakami Y., JP 05-306221, Intestinal Canal Irrigation Solution Composition and Intestinal Canal Irrigation Solution, English Translation (H4-132042), Nelles Translations, 7 pages, (Oct. 21, 2008).
Norgine Pty Ltd, "Deaths and kidney failures call bowel preparation safety into question" United Kingdom, Dec. 17, 2008.
Remington Parmaceutical Sciences (16th edition, Osol, ed, 1980) p. 873.
Ross, et al., Differential Permeability of the Proximal and Distal Rabbit Small Bowel, Journal of Clinical Investigation, vol. 51, Sep. 1972.
Schiller, L.R., Review Article: The Therapy of Constipation, 2001, Alimentary Pharmacology and Therapeutics, vol. 15, pp. 749-763.
Tsuneyuki, O., et al., "Laxative threshold of sugar alcohol erythritol in human subjects," Nutrition Research, 16(4):577-589, Apr. 1996 (Abstract).
Written Opinion, International Application No. PCT/AU2011/001609, dated Dec. 13, 2011.
Written Opinion, International Application No. PCT/AU2012/001315, dated Oct. 27, 2012.
Androgue, Horacio J. et al., "Hyponatremia", The New England Journal of Medicine, May 25, 2000, vol. 342, No. 21, pp. 1581-1590.
Altomare, Donato F. et al., "Colonic Explosion During Diathermy Colotomy", Dis Colon Rectum, Mar. 1993, pp. 291-292.
Arieff, Allen I. et al., "Neurological Manifestations and Morbidity of Hyponatremia: Correlation with Brain Water and Electrolytes", Medicine, vol. 55, No. 2, pp. 121-129, (1976).
Arrigoni et al., "Human gut microbiota does not ferment erythritol", British Journal of Nutrition, 2005, 94:643-646.
Ayus, JC et al., "Treatment of symptomatic hyponatremia and its relation to brain damage. A prospective study," N Engl. J. Med., Nov. 5, 1987, 317(19):1190-5.
Bernt et al., "Erythritol: A Review of Biological and Toxicological Studies", Regulatory Toxicology and Pharmacology, 24, S191-S197 (1996).
Bini EJ et al., "Prospective, randomized, single-blind comparison of two preparations for screening flexible sigmoidoscopy", Gastrointest Endosc Aug. 2000; 52(2) 218-22.
Booth, A.N. et al., "Effects of Prolonged Ingestion of Xylose on Rats", In the Journal of Nutrition, 1953, pp. 347-355.
Bornet et al., "Gastrointestinal Response and Plasma and Urine Determinations in Human Subjects Given Erythritol", Regulatory Toxicology and Pharmacology, 24, S296-S302 (1996).
Borody et al., "A Phase II, Comparative, Single-blinded, Randomised Study to Evaluate the Efficacy and Safety of Hypertonic Solution Combined with PicoPrep™ Capsules Compared with PicoPrep™ Capsules Alone, Standard Glycoprep™ and Standard PicoPrep™ as a Bowel Preparation," Clinical Study Report, Version 1, Jun. 30, 2006, pp. 1-72.
Campbell, Karen, "Why is Everyone Going on About Childhood Overweight and What Can We Do About It?", Nutridate, vol. 18, No. 1, Mar. 2007, pp. 1-9.
Carulli, N. et al., "Absorption of Lactulose in Man", Digestion, 1972, 6:139-145.
Chapman, M.A.S. et al., "Antibacterial activity of bowel-cleansing agents: implications of antibacteroides activity of senna", British Journal of Surgery, 1995, 82, 1053.
Clark, C. Graham et al., "Methods of Cultivation of Luminal Parasitic Protists of Clinical Importance", Clinical Microbiology Reviews, Jul. 2002, vol. 15, No. 3, pp. 329-341.
Cohen, Clemens D. et al., "Hyponatraemia as a complication of colonoscopy", The Lancet, vol. 357, Issue 9252, Jan. 27, 2001, pp. 282-283.
Corazziari, E. et al., "Small Volume Isosmotic Polyethylene Glycol Electrolyte Balanced Solution (PMF-100) in Treatment of Chronic Nonorganic Constipation", Digestive Diseases and Sciences, vol. 41, No. 8, Aug. 1996, pp. 1636-1642.
Dennison, Barbara A., "Fruit Juice Consumption by Infants and Children: A Review", Journal of the American College of Nutrition, vol. 15, No. 5, 4S-11S (1996).
El-Gendy, Nashwa et al., "Dry powdered aerosols of diatrizoic acid nanoparticle agglomerates as a lung contrast agent", International Journal of Pharmaceutics, 391 (2010) pp. 305-312.
Ellegard, L. et al., "Inulin and oligofructose do not influence the absorption of cholesterol, or the excretion of cholesterol, Ca, Mg, Zn, Fe, or bile acids but increases energy excretion in ileostomy subjects", European Journal of Clinical Nutrition, 1997, 51, 1-5.
Fincher, Roger Keith et al., "A Comparison of Bowel Preparations for Flexible Sigmoidoscopy: Oral Magnesium Citrate Combined with Oral Bisacodyl, One Hypertonic Phosphate Enema, or Two Hypertonic Phosphate Enemas", The American Journal of Gastroenterology, vol. 94, No. 8, 1999, pp. 2122-2127.
Fraser, Cosmo L. et al., "Sex differences result in increased morbidity from hyponatremia in female rats", The American Physiological Society, 1989, pp. R880-R884.
Hiele, Martin et al., "Metabolism of erythritol in humans: comparison with glucose and lactitol", British Journal of Nutrition, 1993, 69, 169-176.
Horii, Yakuhin Kogyo KK, "Intestinal rinse soln. contains magnesium citrate, sodium chloride, potassium hydroxide and sugar", Derwent Abstract, Accession C93-181899, 1993.
Hoy et al., "Sodium Picosulfate/Magnesium Citrate: A Review of its Use as a Colorectal Cleanser", Drugs, 69 (1):123-136, Jan. 1, 2009.
IPCS Inchem Home, "Toxicological Evaluation of Some Antimicrobials, Antioxidants, Emulsifiers, Stabilizers, Flour-Treatment Agents, Acids and Bases", FAO Nutrition Meetings Report, 40A,B,C, WHO/Food Add./67.29, 1965.
Izzo et al., "The osmotic and intrinsic mechanisms of the pharmacological laxative action of oral high doses of magnesium sulphate. Importance of the release of digestive polypeptides and nitric oxide", Magnes Res Jun. 1996, 9 (2):133-8.
Lai, Edwin J. et al., "The Boston bowel preparation scale: a valid and reliable instrument for colonoscopy-oriented research," Gastrointestinal Endoscopy, vol. 69, No. 3, Part 2 of 2, 2009, pp. 620-625.

(56) References Cited

OTHER PUBLICATIONS

Liacouras, Piccoli, "Whole-bowel irrigation as an adjunct to the treatment of chronic, relapsing Clostridium difficile colitis", J Clin Gastroenterol Apr. 1996, 22 (3):186-9.
Maksimovais, "Physiological saline-based irrigant for use in eye surgery—contains solutions of calcium, magnesium and potassium chloride(s), phosphate buffer, glucose solution and asorbic acid solution", Derwent Accession No. C98-113774, 1997.
Melton, J.E. et al., "Volume regulatory loss of Na, Cl, and K from rat brain during acute hyponatremia", Am J Physiol 1987; 252:F661-F669.
Munro, Erythritol: An Interpretive Summary of Biochemical, Metabolic, Toxicological and Clinical Data, Food and Chemical Toxicology, 36 (1998) 1139-1174.
Noda et al., "Metabolim and Disposition of Erythritol after Oral Administration to Rats", In the Journal of Nutrition, 1992, pp. 1266-1272.
Belsey, "Deaths and kidney failures call bowel preparation safety into question", Dec. 17, 2008, pp. 1-5, Norgine.
O'Brien Nabors, Lyn, "Alternative Sweeteners", Third Edition, Revised and Expanded, 2001, pp. 1-3.
Parente et al., "Bowel preparation before colonoscopy in the era of mass screening of colo-rectal cancer: A practical approach", ScienceDirect, Digestive and Liver Disease 41(2009) 87-95.
Borody et al., "Electrolyte Purgative", Provisional Application No. PR3461, Mar. 2001.
Swinyard, Ewarl, "Diuretic Drugs", Chapter 49, Remington's, Pharmaceutical Sciences, 1980, p. 873.
Ross, 1972—Can't Open Document.
Schiller, "Review Article: the therapy of constipation", Ailment Pharmacol Ther, 2001, 15:749-763.
Sharma et al., "Randomized, Controlled Comparison of Two Forms of Preparation for Screening Flexible Sigmoidoscopy", The American Journal of Gastroenterology, vol. 92, No. 5, 1997, pp. 809-811.
Song et al., "Recent advances in the biological production of mannitol", Appl Microbiol Biotechnol (2009) 84:55-62.
Tetzloff et al., "Tolerance to Subchronic, High-Dose Ingestion of Erythriol in Human Volunteers", Regulatory Toxicology and Pharmacology, 24: S286-S295 (1996).
Winawer et al., "Colorectal Cancer Screening and Surveillance: Clinical Guidelines and Rationale—Update Based on New Evidence", Gastroenterology, 2003, 124:544-560.
Defang et al, "In Vitro and In Vivo Evaluation of Two Extended Release Preparations of Combination Metformin and Glipizide." Drug Development and Industrial Pharmacy (2005) 31(7):677-85 (abstract).
Huang et al, "Once-daily Propranolol Extended-Release Tablet Dosage Form: Formulation Design and In Vitro/In Vivo Investigation." European Journal of Pharmaceutics and Biopharmaceutics (2004) 58(3):607-14 (abstract).
International Search Report, International Application No. PCT/IB2013/001640, dated Jan. 14, 2014.
International Preliminary Report on Patentability and Written Opinion, International Application No. PCT/IB2013/001640, dated Jan. 27, 2015.
International Preliminary Report on Patentability and Written Opinion, International Application No. PCT/AU2013/000973, dated Mar. 3, 2015.
Kharidia et al, "The Activity of a Small Lytic Peptide PTP-7 on *Staphylococcus aureus* Biofilms." The Journal of Microbiology (2011) 49(4):663-8 (abstract).
Kuksal et al, "Formulation and in vitro, in vivo evaluation of extended-release matrix tablet of Zidovudine: Influence of combination of hydrophilic and hydrophobic matrix formers" AAPS PharmSciTech. Mar. 2006; 7(1): E1-E9.
PHARMGKB, "Pharmacology and Interactions", Mannitol Data Sheet, Download from http://www.pharmgkb.org/do/serve?objId=PA450320&objC1s=drug, Jun. 1, 2010.
Pimentel et al., "Methane, a gas produced by enteric bacteria, slows intestinal transit and augments small intestinal contractile activity" Am. J. Physiol. Gastrointest. Liver Physiol. (2006) 290:G1089-G1095.
Windholz, M. (Editor), Sodium Chlorite, The Merck Index, Ninth Edition, 1976, p. 1111.
Written Opinion, International Application No. PCT/AU2013/000973, dated Nov. 4, 2013.
Written Opinion, International Application No. PCT/IB2013/001640, dated Jan. 14, 2014.
Kohler et al., "Whole gut irrigation and Prepacol laxative preparation for colonoscopy: a comparison", Br. J. Surg., 77:527-529, 1990.
U.S. Appl. No. 13/111,736, filed May 19, 2011.
U.S. Appl. No. 13/539,092, filed Jun. 29, 2012.
U.S. Appl. No. 10/506,728, filed Mar. 4, 2003.
U.S. Appl. No. 13/993,294, filed Dec. 13, 2011.
U.S. Appl. No. 14/353,744, filed Oct. 27, 2012.
U.S. Appl. No. 14/424,515, Pending, filed Aug. 29, 2013.
U.S. Appl. No. 14/417,172, Pending, filed Jul. 26, 2013.
Diamond R. A. et al., "Bisotaxin Acetate and a Postpartum Oral Laxative: A Random Double Blind Controlled Experiment in 106 Subjects", Lancet, vol. 88, No. 1, Jan. 1968, pp. 16-17.
Mortelmans P., "Experience with the Laxative agent bisoxatine diacetate in a radiodiagnostic department" ARS Medici Revue Internationale De Therapie Pratique, vol. 29, No. 2, Jan. 1974, pp. 337-338.
Rider J.A., "Treatment of acute and chronic constipation with bisoxatin acetate and bisacodyl. Double-blind crossover study," Current Therapeutic Research, Excerpta Medica, vol. 13, No. 6, Jun. 1971, pp. 386-392.
Schmidt et al., Laxative effect of 2,2-bis(p-acetoxyphenyl)-3-oxodihydro-1,4-benzoxazine and some related compounds, CAPlus file [STN online], 1963, AN:1963:411398.
The Clinical Report, vol. 24(2):201-214, 1990.

\* cited by examiner

GASTRIC AND COLONIC FORMULATIONS AND METHODS FOR MAKING AND USING THEM

CROSS-REFERENCE TO RELATED APPLICATIONS

This United States utility patent application is the § 371 national phase of PCT international patent application no. PCT/AU2011/001609, having an international filing date of Dec. 13, 2011, which claims benefit of priority to U.S. Provisional Patent Application Ser. No. 61/422,567, filed Dec. 13, 2010. The aforementioned applications are expressly incorporated herein by reference in their entirety and for all purposes.

TECHNICAL FIELD

This invention generally relates to medicine, pharmacology and biochemistry. In alternative embodiments, the invention provides compositions, e.g., formulations or preparations, used for gastric, gastrointestinal and/or colonic treatments or lavage, e.g., orthostatic lavage, e.g., for inducing the purgation (e.g., cleansing) of a gastrointestinal (GI) tract, including a colon; and methods for making and using them. In alternative embodiments, compositions and methods of the invention are used for the amelioration, treatment and/or prevention of constipation or bloating, for the treatment of abdominal pain, particularly non-specific abdominal pain, and diarrhea, including diarrhea caused by a drug side effect, a psychological condition, a disease or a condition such as Crohn's Disease, a poison, a toxin or an infection, e.g., a toxin-mediated traveler's diarrhea. In alternative embodiments, the invention provides pharmaceuticals and products (articles) of manufacture for delivering these compositions and formulations to an individual, e.g., a human or animal.

BACKGROUND

Electrolyte replenishment fluids are a beneficial factor for patients undergoing preparation for colonoscopy. This poses a problem in that most oral rehydration solutions rely on glucose for co-transportation of electrolytes across the brush border of the small bowel utilizing the GLUT1 transport mechanism. Sugars however are known to cause fermentation and production of combustible gases, unacceptable in colonoscopy where the use of electro-cautery during polypectomy may lead to intracolonic explosion.

Due to these concerns there has been an increasing emphasis on maintaining fluid and electrolyte homeostasis in the patient and avoidance of sugars. The challenge for developing safe and effective bowel preparations has thus been to deliver a product that is: tolerable due to acceptable taste and low volume of the preparation; safe by maintaining electrolyte balance and fluid homeostasis; and, able to minimize side effects and lead to better patient acceptance and compliance in consuming the purgative to better clean the bowel.

Several issues have become apparent with the use of conventional sugars used in some current purgatives. In particular, the recorded cases of intra-colonic combustion/explosion secondary to fermentation of the sugars by colon bacteria is a potential problem, although no instances of such complications actually occurred using the described preparations. There were three factors which could contribute to a potential explosion during colonoscopy. These include the remaining colonic bacterial load, propensity of the sugar to produce fermentation products such as methane and hydrogen, and the use of an electro-cautery during colonoscopy. This complication remains a feared but at most but a theoretical problem since only very small quantities of sugar have been incorporated into the purgative compositions described in the past. There is, nevertheless, continuing perception that some non-absorbable sugars such as mannitol or lactulose—may still, potentially pose an explosive potential. In spite of the addition of electrolytes and the addition of such sugars, the side-effect profile—and while much more favorable thane before—still included occasional patients who experienced headaches, suggesting a need for an improved electrolyte delivery system.

In some products, minimally degradable carbohydrates (sugars) are added to the lavage composition to facilitate the physiological balance of coupled 1:1 transport of sodium and glucose in the small intestine so as to reduce electrolyte loss and concomitant fluid shifts. These carbohydrates also have the ability to provide added purgative effect.

Definitions

The following are some definitions that may be helpful in understanding the description of the present invention. These are intended as general definitions and should in no way limit the scope of the present invention to those terms alone, but are put forth for a better understanding of the following description.

Unless the context requires otherwise or specifically stated to the contrary, integers, steps or elements of the invention recited herein as singular integers, steps or elements clearly encompass both singular and plural forms of the recited integers, steps or elements.

Throughout this specification, unless the context requires otherwise, the word "comprise", or variations such as "comprises" or "comprising", will be understood to imply the inclusion of a stated step or element or integer or group of steps or elements or integers, but not the exclusion of any other step or element or integer or group of elements or integers. Thus, in the context of this specification, the term "comprising" means "including principally, but not necessarily solely".

In some embodiments, equivalents are bioequivalent compounds or compositions or compounds or compositions having substantially the same properties, e.g., substantially the same pharmacokinetic and pharmacodynamic properties.

The information provided herein and references cited are provided solely to assist the understanding of the reader, and do not constitute an admission that any or the references or information is prior art to the present invention.

SUMMARY

According to a first aspect of the present invention, there is provided a composition comprising:

(i) (A) a bisacodyl, or pyridin-2-ylmethanediyl)dibenzene-4,1-diyl diacetate, or 4,4'-(pyridin-2-ylmethylene) bis (4,1-phenylene) diacetate, or bioequivalent diphenylmethane or equivalent, or a bisoxatin (or 2,2-bis(4-hydroxyphenyl)-2H-benzo[b][1,4]oxazin-3(4H)-one), or bisoxatin acetate, or equivalent, and/or (B) sodium picosulphate or equivalent;

(ii) an erythritol, or (2R,3S)-butane-1,2,3,4-tetraol, or equivalent isomers, or a sugar or polyol substitute isoforms, or mixtures thereof; and (iii) a pharmaceutically acceptable salt, or a salt acceptable for oral or enteral administration.

According to a second aspect of the present invention, there is provided a product (article) of manufacture comprising a composition of the first aspect.

According to a third aspect of the present invention, there is provided a pharmaceutical composition, a preparation, or a formulation, or food, feed, supplement or additive, comprising a composition of the first aspect.

According to a fourth aspect of the present invention, there is provided a method for performing a colonoscopy; an enteroscopy or endoscopy; a capsule endoscopy; a viewing of the intestinal or colonic mucosa; a surgical or an investigative, therapeutic or ameliorative, prophylactic or radiological procedure involving the intestine or colon; comprising:

(a) administering a composition of the first aspect or a product (article) of manufacture of the second aspect, or a pharmaceutical composition, preparation or formulation, or food, feed, supplement or additive, of the third aspect, to an individual in need thereof.

According to a fifth aspect of the present invention, there is provided a method for the amelioration, treatment and/or prevention of constipation or bloating, for the treatment of abdominal pain, particularly non-specific abdominal pain, and diarrhea, including diarrhea caused by a drug side effect, a psychological condition, a disease or a condition such as Crohn's Disease, a poison, a toxin or an infection, e.g., a toxin-mediated traveler's diarrhea, comprising administering a composition of the first aspect, or a product (article) of manufacture of the second aspect, or a pharmaceutical composition, preparation or formulation, or food, feed, supplement or additive, of the third aspect to an individual in need thereof.

According to a sixth aspect of the present invention, there is provided a method for the amelioration or treatment of a bowel disease, comprising administering a composition of the first aspect or a product (article) of manufacture of the second aspect, or a pharmaceutical composition, preparation or formulation, or food, feed, supplement or additive, of the third aspect, to an individual in need thereof.

According to a seventh aspect of the present invention, there is provided a method for the amelioration or treatment of a bowel disease or condition having a bowel dysfunction component, an inflammatory bowel disease (IBD), Crohn's disease, a hepatic encephalopathy, an enteritis, a colitis, an irritable bowel syndrome (IBS), a fibromyalgia (FM), a chronic fatigue syndrome (CFS), a depression, an attention deficit/hyperactivity disorder (ADHD), a multiple sclerosis (MS), a systemic lupus erythematosus (SLE), a travelers' diarrhea, a small intestinal bacterial overgrowth, a chronic pancreatitis, or a pancreatic insufficiency, comprising administration of therapeutically effective amount of the composition of the first aspect, or a product (article) of manufacture of the second aspect, or a pharmaceutical composition, preparation or formulation, or food, feed, supplement or additive, of the third aspect, to an individual in need thereof.

According to an eighth aspect of the present invention, there is provided a package or kit comprising combination of at least two formulations, wherein one (a first) formulation is contained in a first container and a second formulation is contained in a second container, and the formulations are designed to be taken in sequence as part of a treatment or colonoscopy preparation regimen, wherein a patient is administered or instructed to take the contents of a first container before the contents of a second container, wherein the first or second formulation is a composition of the first aspect or a product (article) of manufacture of the second aspect, or a pharmaceutical composition, preparation or formulation, or food, feed, supplement or additive, of the third aspect.

According to a tenth aspect of the present invention, there is provided a method for administering a combination of (at least two) different formulations that are designed to be taken in as part of a treatment or a colonoscopy preparation regimen, comprising administering the contents of the first container, then several hours later or the next day the contents of the second container, wherein the first and second container are in the package or kit of the eighth aspect.

According to an eleventh aspect of the present invention, there is provided a pharmaceutical composition, a preparation, or a formulation comprising a composition of the first aspect or a product (article) of manufacture of the second aspect, or a pharmaceutical composition, preparation or formulation, or food, feed, supplement or additive, of the third aspect, wherein the pharmaceutical composition, a preparation, or a formulation is manufactured, labeled or formulated for the amelioration or treatment of a bowel disease, wherein optionally the bowel disease or condition having a bowel dysfunction component, comprises: an inflammatory bowel disease (IBD), Crohn's disease, hepatic encephalopathy, enteritis, colitis, irritable bowel syndrome (IBS), fibromyalgia (FM), chronic fatigue syndrome (CFS), depression, attention deficit/hyperactivity disorder (ADHD), multiple sclerosis (MS), systemic lupus erythematosus (SLE), travelers' diarrhea, small intestinal bacterial overgrowth, chronic pancreatitis, or a pancreatic insufficiency.

According to a twelfth aspect of the present invention, there is provided use of a composition of the first aspect or a product (article) of manufacture of the second aspect, or a pharmaceutical composition, preparation or formulation, or food, feed, supplement or additive, of the third aspect, for manufacture of a medicament.

According to a thirteenth aspect of the present invention, there is provided use of a composition of the first aspect or a product (article) of manufacture of the second aspect, or a pharmaceutical composition, preparation or formulation, or food, feed, supplement or additive, of the third aspect, in the preparation of a medicament for the amelioration, treatment and/or prevention of constipation or bloating, for the treatment of abdominal pain, particularly non-specific abdominal pain, and diarrhea, including diarrhea caused by a drug side effect, a psychological condition, a disease or a condition such as Crohn's Disease, a poison, a toxin or an infection, e.g., a toxin-mediated traveler's diarrhea.

According to a fourteenth aspect of the present invention, there is provided use of a composition of the first aspect or a product (article) of manufacture of the second aspect or a pharmaceutical composition, preparation or formulation, or food, feed, supplement or additive, of the third aspect, in the preparation of a medicament for the amelioration or treatment of a bowel disease, wherein optionally the bowel disease or condition having a bowel dysfunction component, comprises: an inflammatory bowel disease (IBD), Crohn's disease, hepatic encephalopathy, enteritis, colitis, irritable bowel syndrome (IBS), fibromyalgia (FM), chronic fatigue syndrome (CFS), depression, attention deficit/hyperactivity disorder (ADHD), multiple sclerosis (MS), systemic lupus erythematosus (SLE), travelers' diarrhea, small intestinal bacterial overgrowth, chronic pancreatitis, or a pancreatic insufficiency.

According to a fifteenth aspect of the present invention, there is provided a composition of the first aspect or a product (article) of manufacture of the second aspect, or a pharmaceutical composition, preparation or formulation, or food, feed, supplement or additive, of the third aspect, for use in the amelioration, treatment and/or prevention of constipation or bloating, for use in the treatment of abdominal pain, particularly non-specific abdominal pain, and diarrhea, including diarrhea caused by a drug side effect, a psychological condition, a disease or a condition such as Crohn's Disease, a poison, a toxin or an infection, e.g., a toxin-mediated traveler's diarrhea.

According to a sixteenth aspect of the present invention, there is provided a composition of the first aspect or a product (article) of manufacture of the second aspect, or a pharmaceutical composition, preparation or formulation, or food, feed, supplement or additive, of the third aspect, for use in the amelioration or treatment of a bowel disease, wherein optionally the bowel disease or condition having a bowel dysfunction component, comprises: an inflammatory bowel disease (IBD), Crohn's disease, hepatic encephalopathy, enteritis, colitis, irritable bowel syndrome (IBS), fibromyalgia (FM), chronic fatigue syndrome (CFS), depression, attention deficit/hyperactivity disorder (ADHD), multiple sclerosis (MS), systemic lupus erythematosus (SLE), travelers' diarrhea, small intestinal bacterial overgrowth, chronic pancreatitis, or a pancreatic insufficiency.

In alternative embodiments, the invention provides compositions (including formulations, pharmaceutical compositions, foods, feeds, supplements, products of manufacture, and the like, and methods for making and using them) comprising:

(a) (i) (A) a bisacodyl, or (pyridin-2-ylmethanediyl)dibenzene-4,1-diyl diacetate, or 4,4'-(pyridin-2-ylmethylene) bis(4,1-phenylene) diacetate, or bioequivalent diphenylmethane or equivalent or a bisoxatin (or 2,2-bis(4-hydroxyphenyl)-2H-benzo[b][1,4]oxazin-3(4H)-one), or bisoxatin acetate, or equivalent, wherein optionally the composition comprises between about 1, 5, 10, 15, 20, 25, 30, 35, 40, 45 to 50 milligram (mg) to about 100, 150, 200, 240, 250, 300, 350, 400, 450, 500, 550, 600, 650, 700, 750, 800, 850, 900, 950 or 1000 or more milligrams (mg), or between about 5 milligrams (mg) to about 15 milligrams (mg), or the composition comprises about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 105, 110, 115, 120, 130, 140, 150, 160, 170, 180, 190, 200, 210, 220, 230, 240, 250, 275, 300, 350, 400, 450 or 500 or more mgs of:

a bisacodyl, or (pyridin-2-ylmethanediyl)dibenzene-4,1-diyl diacetate, or 4,4'-(pyridin-2-ylmethylene) bis(4,1-phenylene) diacetate, or bioequivalent diphenylmethane or equivalent, or a bisoxatin (or 2,2-bis(4-hydroxyphenyl)-2H-benzo[b][1,4]oxazin-3(4H)-one), or bisoxatin acetate, or equivalent, or wherein optionally the composition comprises between about 5, 10, 20, 30, 40, or 50 mg to about 1, 2, 3, 4, 5, 6, 7, 8, 9 or 10 or more grams (g) of a bisacodyl or (pyridin-2-ylmethanediyl)dibenzene-4,1-diyl diacetate, or 4,4'-(pyridin-2-ylmethylene) bis(4,1-phenylene) diacetate, or bioequivalent diphenylmethane or equivalent or a bisoxatin (or 2,2-bis(4-hydroxyphenyl)-2H-benzo[b][1,4]oxazin-3(4H)-one), or bisoxatin acetate, or equivalent, or between about 75, 80, 85, 90 or 100 mg to about 150 to 200 mg (optionally, for a normal patient) bisacodyl or pyridin-2-ylmethanediyl) dibenzene-4,1-diyl diacetate, or 4,4'-(pyridin-2-ylmethylene) bis(4,1-phenylene) diacetate, or bioequivalent diphenylmethane or equivalent or a bisoxatin (or 2,2-bis(4-hydroxyphenyl)-2H-benzo[b][1,4]oxazin-3(4H)-one), or bisoxatin acetate, or equivalent, or between about 100, 110, 120, 130, 140 or 150 mg to about 1, 2, 3, 4 or 4.5 g or more bisacodyl or pyridin-2-ylmethanediyl)dibenzene-4,1-diyl diacetate, or 4,4'-(pyridin-2-ylmethylene) bis(4,1-phenylene) diacetate, or bioequivalent diphenylmethane or equivalent or a bisoxatin (or 2,2-bis(4-hydroxyphenyl)-2H-benzo[b][1,4]oxazin-3(4H)-one), or bisoxatin acetate, or equivalent for a constipated patient, of:

a bisacodyl, or (pyridin-2-ylmethanediyl)dibenzene-4,1-diyl diacetate, or 4,4'-(pyridin-2-ylmethylene) bis(4,1-phenylene) diacetate, or bioequivalent diphenylmethane or equivalent, oror a bisoxatin (or 2,2-bis(4-hydroxyphenyl)-2H-benzo[b][1,4]oxazin-3(4H)-one), or bisoxatin acetate, or equivalent, wherein optionally the composition comprises between about 10, 20, 30, 40, 50, 75, 80, 85, 90, 100 or 150 mg to about 100, 150, 200, 250, 300, 350, 400, 450, or 500 or more mg, or between about 50, 75, 80, 85, 90, 100, or 150 mg to about 150 to 200 mg (e.g., for a normal patient), or between about 100 to 250 mg, or between about 100, 110, 120, 130, 140 or 150 mg to about 1, 2, 3, 4 or 4.5 g or more for a constipated patient, of a bisacodyl, or (pyridin-2-ylmethanediyl)dibenzene-4,1-diyl diacetate, or 4,4'-(pyridin-2-ylmethylene) bis(4,1-phenylene) diacetate, or bioequivalent diphenylmethane or equivalent or a bisoxatin (or 2,2-bis(4-hydroxyphenyl)-2H-benzo[b][1,4]oxazin-3(4H)-one), or bisoxatin acetate, or equivalent, or (A1) a bisacodyl, or pyridin-2-ylmethanediyl)dibenzene-4,1-diyl diacetate, or 4,4'-(pyridin-2-ylmethylene) bis(4,1-phenylene) diacetate, or bioequivalent diphenylmethane, at or less than about 25 mg, 24 mg, 23 mg, 22 mg, 21 mg, 20 mg, 19 mg, 18 mg, 17 mg, 16 mg, 15 mg, 14 mg, 13 mg, 12 mg, 11 mg, 10 mg, 9 mg, 8 mg, 7 mg, 6 mg, 5 mg, 4 mg, 3 mg, 2 mg or 1 mg or less, or are between about 1 and 25 mg per dosage;

and optionally the bisacodyl is DULCOLAX™, DUROLAX™, FLEET™, ALOPHEN™ or CORRECTOL™; and optionally the bisoxatin is LAXONALIN™, MARATAN™, TALSIS™, TASIS™, WYLAXINE™ and/or (B) a sodium picosulphate or equivalent, wherein optionally the composition comprises between about 1 milligram (mg) to about 100 milligrams (mg), or between about 5 milligrams (mg) to about 15 milligrams (mg), or the composition comprises about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 or more mgs of a sodium picosulphate or equivalent;

(ii) an erythritol, or (2R,3S)-butane-1,2,3,4-tetraol, or equivalent isomers or sugar or polyol substitute isoforms, wherein optionally the composition comprises between about 1 to about 40 grams of erythritol (or equivalent isomers or sugar substitute or synthetic isoforms); or, about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 or more grams, of erythritol (or equivalent isomers or sugar substitute or synthetic isoforms); and (iii) a pharmaceutically acceptable salt, or a salt acceptable for oral or enteral administration;

wherein optionally the composition comprises between about 1 to about 40 grams, or between about 8 to 15 grams, or between about 15 to 28 grams, of salt or salts per day; or, about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 or more grams, of salt or salts, wherein the composition is formulated for uses as a purgative, a colonic cleanser, or for orthostatic lavage; or (b) the composition of (a), wherein:

(1) (i) the salt is a water-soluble salt; (ii) optionally the erythritol, equivalent isomer or sugar or polyol substitute isoform, is present in an amount, by weight, of from about 1 to about 3 times the weight of the salt ions in (each unit dose of) the composition; (iii) optionally the salt comprises a water-soluble potassium salt in an amount, by weight, of from about 0.05 to about 1 times the weight of a sodium salt in the composition; or (iv) optionally the salt comprises a water-soluble magnesium salt, wherein the weight of magnesium ions in the composition is from about 0.1 to about 10 times the weight of sodium ions in the composition; or (2) the salt comprises at least one of a calcium salt, a calcium carbonate, a calcium acetate, a citrate salt, a calcium citrate, a magnesium salt, a magnesium sulphate, a magnesium citrate, a monobasic sodium phosphate, dibasic sodium phosphate, and/or tribasic sodium phosphate, a magnesium phosphate, a sodium salt, a sodium sulphate, a sodium chloride, a sodium gluconate, a sodium citrate, a sodium aspartate, a potassium salt, a potassium gluconate, a potassium tartrate, a potassium chloride, an acetate salt, an adipate salt, an alginate salt, an aspartate salt, a benzoate salt, a benzenesulfonate salt, a bisulfate salt, a butyrate salt, a camphorate salt, a camphor sulfonate salt, a digluconate salt, a glycerophosphate salt, a hemisulfate salt, a heptanoate salt, a hexanoate salt, a fumarate salt, a hydrochloride salt, a hydrobromide salt, a hydroiodide salt, a 2-hydroxyethansulfonate (isothionate) salt, a lactate salt, a maleate salt, a methane sulfonate salt, a nicotinate salt, a 2-naphthalene sulfonate salt, an oxalate salt, a palmitoate salt, a pectinate salt, a persulfate salt, a 3-phenylpropionate salt, a picrate salt, a pivalate salt, a propionate salt, a succinate salt, a tartrate salt, a thiocyanate salt, a phosphate salt, a glutamate salt, a bicarbonate salt, a p-toluenesulfonate salt, a undecanoate salt, or any equivalent salt, or any salt as described in "Handbook of Pharmaceutical Salts: Properties, Selection and Use", Weinheim, N.Y.: VHCA; Wiley-VCH, 2002, or any mixture thereof;

(c) the composition of (a) or (b), wherein the composition is manufactured, labeled or formulated as a liquid, a suspension, a spray, a gel, a geltab, a semisolid, a tablet, a lozenge, a sachet or a capsule;

(d) the composition of any of (a) to (c), wherein the composition is manufactured, labeled or formulated as a preparation, a pharmaceutical or a formulation for human or animal use;

(e) the composition of (d), wherein the animal use is for a veterinary use; or (f) the composition of any of (a) to (e), wherein the composition is manufactured, labeled or formulated for use as a purgative, or for orthostatic lavage.

In alternative embodiments, a composition of the invention further comprises:

(a) a defoaming agent, a surfactant agent, a lubricant, an acid neutralizer, a marker, a cell marker, a drug, an antibiotic and/or a contrast agent;

(b) the composition of (a), wherein the marker comprises a hexaminolevulinate, an indigo carmine or a methylene blue or an equivalent cell marker;

(c) the composition of (a), wherein the marker comprises an antibody specific for a normal or abnormal cell phenotype or genotype, or a cancer cell or a polyp;

(d) the composition of (a), wherein the surfactant agent comprises a simethicone or any mixture of polydimethylsiloxane and silica gel, or equivalent;

(e) the composition of (a), wherein the lubricant comprises a magnesium stearate, a hyaluronic acid, a glycerol and/or a silicone, and/or the lubricant comprises an encapsulating material, wherein the encapsulating material acts as a capsule or covering for a preparation of the composition;

(f) the composition of (a), wherein the defoaming agent comprises a silicone and/or a glycerol;

(g) the composition of (f), wherein the acid neutralizer comprises a water-soluble acid neutralizer, which optionally comprises a tromethamine, a meglumine, a sodium bicarbonate, a sodium carbonate, or any combination thereof, or the acid neutralizer comprises a water-insoluble acid neutralizer, which optionally comprises a magnesium hydroxide, an aluminum hydroxide, a dihydroxy aluminum sodium carbonate, a calcium carbonate, and any combination thereof;

(h) the composition of (a), wherein the antibiotic is one or more of a rifamycin, aminoglycoside, amphenicol, ansamycin, beta-lactam, carbapenem, cephalosporin, cephamycin, monobactam, oxacephem, a lincosamide antibiotic (e.g., clindamycin, lincomycin), a macrolide antibiotic (e.g., an azithromycin, clarithromycin, dirithromycin, erythromycin), glycopeptide antibiotic (e.g., a vancomycin, teicoplanin, televancin, bleomycin, ramoplanin and/or a decaplanin), a polypeptide antibiotic (e.g., actinomycin, such as actinomycin D; bacitracin), tetracycline, or a 2,4-diaminopyrimidine class antibiotic;

(i) the composition of any of (a) to (h), further comprising at least one non-osmotic purgative, which optionally comprises a mineral oil, aloe, bisoxatin, bisacodyl, sodium picosulfate or equivalent, casanthranol, cascara, castor oil, danthron, dehydrocholic acid, phenolphthalein, sennosides, docusate, bethanachol, colchicines, misoprostol, cisapride, norcisapride, paraffin, rhein and/or tegaserod or equivalents; and/or further comprising at least one bulk-forming purgative, which optionally comprises a methylcellulose, sodium carboxymethyl cellulose, bran, psyllium, sterculia and/or testa ispaghula or equivalents;

(j) the composition of any of (a) to (i), further comprising at least one halogenated carbohydrate, which optionally comprises a halogenated monosaccharide, halogenated polysaccharide, halogenated oligosaccharide, halogenated disaccharide, and/or halogenated trisaccharide, wherein the halogen optionally comprises a fluorine, chlorine, bromine, iodine, and/or an astatine;

(k) the composition of any of (a) to (j), further comprising at least one dispersal agent, buffering agent, sweetening agent, debittering agent, flavoring agent, pH stabilizer, acidifying agent, preservative, desweetening agent and/or coloring agent; or (l) the composition of any of (a) to (i), further comprising at least one disintegrant, which optionally comprises a natural starch, a maize starch or potato starch; a directly compressible starch; a modified or pre-gelatinized starch, a carboxymethyl starch, a sodium starch glycolate; a natural or a chemically-modified cellulose, a crosslinked sodium carboxymethyl cellulose, a croscarmellose sodium, a low substituted hydroxypropyl cellulose; a microcrystalline cellulose; a gum, an agar gum, a guar gum; an alginic acid or salts thereof; an acetate or a citrate; an aluminum oxide; a synthetic polymer, a cross-linked polyvinylpyrrolidone and/or a crospovidone; or (m) the composition of any of (a) to (l), further comprising at least one vitamin, mineral and/or dietary supplement, wherein optionally the vitamin comprises a thiamine, riboflavin, nicotinic acid, pantothenic acid, pyridoxine, biotin, folic acid, vitamin $B_{12}$, lipoic acid, ascorbic acid, vitamin A, vitamin D, vitamin E, vitamin K, a choline, a carnitine, and/or an alpha, beta and/or gamma carotene.

In alternative embodiments, the invention provides a product (article) of manufacture comprising a composition of the invention.

In alternative embodiments, the invention provides a pharmaceutical composition, a preparation, or a formulation, or a feed, food or supplement, comprising a composition of the invention. In alternative embodiments, the pharmaceutical composition, preparation, formulation, feed, food or supplement comprises:

(a) a composition of the invention;

(b) the pharmaceutical composition, preparation or formulation of (a), wherein the composition is manufactured, labeled or formulated as a liquid, a suspension, a gel, a geltab, a semisolid, a tablet, a sachet, a lozenge or a capsule, or as an enteral formulate;

(c) the pharmaceutical composition, preparation or formulation of (a) or (b), wherein the pharmaceutical composition or a formulation is manufactured with an encapsulating material, and optionally the encapsulating material comprises a lubricant;

(d) the pharmaceutical composition, a preparation, or a formulation of any of (a) to (c), wherein the pharmaceutical composition, a preparation, or a formulation is manufactured, labeled or formulated for human or animal use;

(e) the pharmaceutical composition, a preparation, or a formulation of (d), wherein the animal use is for a veterinary use;

(f) the pharmaceutical composition, a preparation, or a formulation of any of (a) to (e), wherein the pharmaceutical composition, a preparation, or a formulate is manufactured, labeled or formulated for use as a purgative, or for orthostatic lavage; or for use with (e.g., in preparation for) a colonoscopy; an enteroscopy or endoscopy; a capsule endoscopy; a viewing of the intestinal or colonic mucosa; a surgical or an investigative, therapeutic or ameliorative, prophylactic or radiological procedure involving the intestine or colon;

(g) the pharmaceutical composition, a preparation, or a formulation of any of (a) to (e), wherein the pharmaceutical composition, a preparation, or a formulation is manufactured, labeled or formulated for the amelioration, treatment and/or prevention of constipation or bloating, for the treatment of abdominal pain, particularly non-specific abdominal pain, and diarrhea, including diarrhea caused by a drug side effect, a psychological condition, a disease or a condition such as Crohn's Disease, a poison, a toxin or an infection, e.g., a toxin-mediated traveler's diarrhea; or (h) the pharmaceutical composition, a preparation, or a formulation of any of (a) to (e), wherein the pharmaceutical composition, a preparation, or a formulation is manufactured, labeled or formulated for the amelioration or treatment of a bowel disease, wherein optionally the bowel disease or condition having a bowel dysfunction component, comprises: an inflammatory bowel disease (IBD), Crohn's disease, hepatic encephalopathy, enteritis, colitis, irritable bowel syndrome (IBS), fibromyalgia (FM), chronic fatigue syndrome (CFS), depression, attention deficit/hyperactivity disorder (ADHD), multiple sclerosis (MS), systemic lupus erythematosus (SLE), travelers' diarrhea, small intestinal bacterial overgrowth, chronic pancreatitis, or a pancreatic insufficiency.

The invention provides methods for performing a colonoscopy; an enteroscopy or endoscopy; a capsule endoscopy; a viewing of the intestinal or colonic mucosa; a surgical or an investigative, therapeutic or ameliorative, prophylactic or radiological procedure involving the intestine or colon; comprising:

(a) administering a composition of the invention, or a product (article) of manufacture of the invention, or a pharmaceutical composition, preparation or formulation, of food, feed or supplement, of the invention, to an individual in need thereof; or (b) the method of (a), wherein the individual is a human or an animal.

The invention provides methods for the amelioration, treatment and/or prevention of constipation or bloating, for the treatment of abdominal pain, particulary non-specific abdominal pain, and diarrhea, including diarrhea caused by a drug side effect a psychological condition, a disease or a condition such as Crohn's Disease, a poison, a toxin or an infection, e.g., a toxin-mediated traveler's diarrhea, comprising administering a composition of the invention, or a product (article) of manufacture of the invention, or a pharmaceutical composition, preparation or formulation of the invention, to an individual in need thereof.

In alternative embodiments, the constipation or bloating is due to at least one of: travel; change in daily routine; lack of exercise; immobility caused by injury, illness, or aging; dehydration; irritable bowel syndrome; pregnancy; diabetes; hypothyroidism; hypercalcemia; cancer of the colon or rectum; uterine prolapse; vaginal vault prolapse; rectal prolapse; scarring from surgery; injury of the colon or rectum; Parkinson's disease; multiple sclerosis, stroke; hemorrhoids or anal fissures; delaying bowel movements; anxiety; depression; eating disorders; and/or obsessive-compulsive disorder, coeliac disease, muscular dystrophy; myotonic dystrophy, non-specific abdominal pain, or a neurological condition or any cause of constipation.

The invention provides methods for the amelioration or treatment of a bowel disease comprising use of a composition of the invention, wherein optionally the bowel disease or condition having a bowel dysfunction component, comprises: an inflammatory bowel disease (IBD), Crohn's disease, hepatic encephalopathy, enteritis, colitis, irritable bowel syndrome (IBS), fibromyalgia (FM), chronic fatigue syndrome (CFS), depression, attention deficit/hyperactivity disorder (ADHD), multiple sclerosis (MS), systemic lupus erythematosus (SLE), travelers' diarrhea, small intestinal bacterial overgrowth, chronic pancreatitis, or a pancreatic insufficiency.

The invention provides packages or kits (or equivalents) comprising a combination of at least two formulations, wherein one (a first) formulation contained in a first container (e.g., a bottle or blister pack or equivalent) and a second formulation is contained in a second container (e.g., a bottle or blister pack or equivalent), and the formulations are designed to be taken in sequence as part of a treatment or colonoscopy preparation regimen, wherein a patient is administered or instructed to take the contents of a first container (e.g., a bottle, blister pack, and the like) before the contents of a second container.

In alternative embodiments of the packages or kits, the contents of the first container comprises or consists of capsules (or pills, tablets, geltabs, and the like) comprising the following formulation: Bisacodyl or Bisoxatin, Magnesium sulphate, Sodium sulphate, Potassium gluconate, Sodium chloride and Erythritol, optionally in the following exemplary amounts:

First Container

| Bisacodyl or Bisoxatin | 10 mg |
|---|---|
| Magnesium sulphate | 2.95 g |
| Sodium sulphate | 6.32 g |
| Potassium gluconate | 1.26 g |
| Sodium chloride | 1.26 g |
| Erythritol | 1.26 g | and optional these capsules are a different color and/or shape than the capsules (or pills, tablets, geltabs, and the like) in the second formulation (contained in the second container), and optionally the first container (e.g., a bottle) comprises between about 10 to 40 or more capsules, e.g., 10, 11, 12, 13, 14, 15, 16, 17, 18, 19, 20, 21, 22, 23, 24, 25, 26, 27, 28, 29, 30, 31, 32 or more capsules.

In alternate embodiments of the packages or kits, the contents of the second container comprises or consists of capsules (or pills, tablets, geltabs, and the like) comprising the following formulation: Magnesium sulphate, Sodium sulphate, Potassium gluconate, Sodium chloride and Erythritol, optionally in the following exemplary amounts:

Second Container

| Magnesium sulphate | 4.05 g |
|---|---|
| Sodium sulphate | 8.68 g |
| Potassium gluconate | 1.74 g |
| Sodium chloride | 1.74 g |
| Erythritol | 1.74 g, | and optionally the second container comprises between about 2 to 30 or more capsules, e.g., 2, 3, 4, 5, 8, 7, 8, 9, 10, 11, 12, 13, 14, 15, 16, 17, 18, 19, 20, 21, 22, 23, 24, 25, 26, 27, 28, 29, 30, 31, 32 or more capsules.

In alternative embodiments of the packages or kits, the kits comprise a single container that comprises or consists of capsules (or pills, tablets, geltabs, and the like) comprising the following formulation: Bisoxatin, Magnesium sulphate, Sodium sulphate, Potassium gluconate, Sodium chloride and Erythritol, optionally in the following exemplary amounts:

| Bisoxatin | 240 mg |
|---|---|
| Magnesium sulphate | 7 gm |
| Sodium sulphate | 3 gm |
| Potassium gluconate | 3 gm |
| Sodium chloride | 4 gm |
| Erythritol | 2 gm | and optionally the container (e.g., a bottle) comprises between about 10 to 40 or more capsules, e.g., 10, 11, 12, 13, 14, 15, 16, 17, 18, 19, 20, 21, 22, 23, 24, 25, 26, 27, 28, 29, 30, 31, 32 or more capsules.

In alternative embodiments of the packages or kits, the contents of the second container comprises or consists of capsules (or pills, tablets, geltabs, and the like) comprising the following formulation: Magnesium sulphate, Sodium sulphate, Potassium gluconate, Sodium chloride and Erythritol, optionally in the following exemplary amounts:

Second Container

| Magnesium sulphate | 4.05 g |
|---|---|
| Sodium sulphate | 8.68 g |
| Potassium gluconate | 1.74 g |
| Sodium chloride | 1.74 g |
| Erythritol | 1.74 g, | and optionally the second container would have between about 2 to 30 or more capsules, e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or more capsules.

The invention provides methods for administering a combination of (at least two) different formulations that are designed to be taken in sequence (a so-called "split protocol") as part of a treatment or a colonoscopy preparation regimen, comprising administering (or instructing to the patient to self-administer) the contents of the first container, then several hours later (e.g., between about 6 to 24 hours later) or the next day (e.g., the morning of the procedure, e.g., a colonoscopy) the contents of the second container, wherein the first and second container are in the package or kit of the invention, and optionally, the first container (e.g., a bottle) comprises capsules (or pills, tablets, geltabs, and the like) has exemplary formulation 11, and the second container (e.g., a bottle) comprises capsules (or pills, tablets, geltabs, and the like) having exemplary formulation 12, and the first container has about 16 capsules to be taken or administered first, and the second container has about 22 capsules to be taken later, e.g., several hours later between about 6 to 24 hours later) or the next day (e.g., the morning of the procedure, e.g., a colonoscopy), and optionally, the first container comprises capsules (or pills, tablets, geltabs, and the like) having exemplary formulation 11, and the second container comprises capsules (or pills, tablets, geltabs, and the like) having exemplary formulation 12, and the first container has about 32 capsules to be taken or administered first, and the second container (e.g., a bottle) has about 6 capsules to be taken later, e.g., several hours later (e.g., between about 6 to 24 hours later) or the next day (e.g., the morning of the procedure, e.g., a colonoscopy).

The details of one or more embodiments of the invention are set forth in the description below. Other features, objects, and advantages of the invention will be apparent from the description and from the claims.

All publications, patents, patent applications cited herein are hereby expressly incorporated by reference for all purposes.

DETAILED DESCRIPTION

In alternative embodiments, the invention provides compositions, e.g., formulations and pharmaceutical preparations, used for gastric, gastrointestinal and/or colonic treatments or lavage, e.g., orthostatic lavage, e.g., for inducing the purgation (e.g., cleansing) of a gastrointestinal (GI) tract, including a colon; and methods for making and using them. In alternative embodiments, compositions and methods of the invention are used for the amelioration, treatment and/or prevention of constipation or bloating, for the treatment of abdominal pain, particularly non-specific abdominal pain, and diarrhea, including diarrhea caused by a drug side effect, a psychological condition, a disease or a condition such as Crohn's Disease, a poison, a toxin or an infection, e.g., a toxin-mediated traveler's diarrhea. In alternative embodiments, the invention provides pharmaceutical and products (articles) of manufacture for delivering these compositions and formulations to an individual, e.g., a human or an animal.

In alternative embodiments, the invention provides compositions composing the four-carbon (4-carbon) chain polyol known as erythritol, or (2R,3S)-butane-1,2,3,4-tetraol, or equivalent isomers or sugar or polyol substitute isoforms, and low dosages of bisacodyl or a bisoxatin.

In one embodiment, the erythritol is produced from glucose by fermentation with a yeast such as *Moniliella pollinis*. Erythritol demonstrates none or minimal fermentation by colonic bacteria and only non-combustible short chain fatty acids and $CO_2$ are produced in small amounts, see e.g., Noda (1992) J. Nutri 122:1266-1272. There have been no recorded significant human gastroenterological side effects at erythritol doses of up to 1000 mg/kg body weight/day. Absorbed erythritol is not metabolized systemically and is excreted unchanged in urine, further improving its safety profile as it will not cause interactions or cause metabolic disturbances. Erythritol has no effect on 24 hour output of creatinine, urea or electrolytes (e.g., sodium, potassium, chloride, phosphate)—in direct contrast to phosphate lavage preparations.

In alternative embodiments, the "low" dosages of bisacodyl are at or less than about 25 mg, 24 mg, 23 mg, 22 mg, 21 mg, 20 mg, 19 mg, 18 mg, 17 mg, 16 mg, 15 mg, 14 mg, 13 mg, 12 mg, 11 mg, 10 mg, 9 mg, 8 mg, 7 mg, 6 mg, 5 mg, 4 mg, 3 mg, 2 mg or 1 mg or less, or are between about 1 and 25 mg per dosage. When erythritol is added to a purgative agent such as bisacodyl, which promotes evacuation of the colon by altering intestinal fluid and electrolyte absorption and smooth muscle contractility, we have discovered an unexpected enhanced purgative action. Bisacodyl has on rare occasions been associated with ischemic colitis in doses of 20 mg, and less frequently with the 10 mg tablet form in combination with HALFLYTELY™ (Braintree Labs, Braintree, Mass.). No ischemic colitis has been consistently observed or reported using bisacodyl in spite of its widespread chronic use at a lower dosage range often on a daily basis for treatment of constipation or bloating over long periods.

In alternative embodiments, additional ingredients, reagents, agents and/or biologies are included in a composition of the invention. For example, a composition, e.g., a purgative of the invention for colonic lavage, designed or manufactured as a vehicle for the delivery of one or more markers, e.g., markers that can highlight the presence of a normal or an abnormal cell type, e.g., a colonic polyp. This embodiment allows for a higher detection rate of polyps during a colonoscopy.

In one embodiment, a hexaminolevulinate is added to a composition of the invention to mark polyps with fluorescence, e.g., prior to a colonoscopy, so as to facilitate enhanced polyp detection. An appropriate blue excitation light of 375-440 nm can be used. This preparation of the invention can enhance the value of the bowel preparation by also improving the polyp detection rate, as has been found in the case of bladder cancers using this marker. In alternative embodiments, other markers such as indigo carmine or methylene blue are similarly incorporated into a formulation of the invention, e.g., to further improve colonic polyp detection rates without the need for 'blue-light' colonoscopy.

In one embodiment, adequate visualization of the bowel lumen of a colon is further enhanced by addition of a simethicone or similar surfactant agent to a formulation or preparation of the invention. This can reduce bubbling often seen at colonoscopy that obscures visualization.

In one embodiment, a lubricant is added to a formulation or preparation of the invention to e.g. facilitate the passage of a colonoscopy by reducing mucosal resistance. In alternative embodiments, lubricants used in formulations or preparations of the invention comprise hyaluronic acid, glycerol and/or silicone. In one embodiment, an encapsulating substance dissolves in the gut to form a lubricant; as in one alternative aspect there can be between about 20 to 40 capsules (or other unit dosage form, e.g., a geltab, tablet, etc.) administered. In one embodiment, a specialised encapsulating material is used as a lubricant.

Silicones that can be used to manufacture formulations or preparations of the invention are polymers that include silicon together with carbon, hydrogen, oxygen, and sometimes other chemical elements; and can have a thermal stability, e.g., a constancy of properties over a wide operating range of between about −100 to 250° C.; and, although not a hydrophobe, silicon is able to repel water and does not stick. With low chemical reactivity and low toxicity, silicone does not support microbiological growth. During polymerization, this reaction can evolve a hazardous hydrogen chloride gas. For medical uses, the invention can use a process where the chlorine atoms in the silane precursor are replaced with acetate groups. In one aspect, silicones are used as a defoamer because of a low water solubility and good spreading properties. In one aspect, gelatin capsules incorporating glycerol are used; they can further assist as a lubricant and defoamer.

From systematic clinical studies we have now discovered that a lavage-powdered composition comprising stimulants such as bisacodyl or sodium picosulphate or a bisoxatin, at least one of various salts e.g. magnesium sulphate, sodium sulphate, potassium gluconate, and the polyol erythritol (or (2R,3S)-butane-1,2,3,4-tetraol) or equivalents, is not only capable of cleansing the bowel effectively while using a small number of capsules but has other major improvement features. It maintains its hypertonicity when it dissolves in the stomach and when it is followed by the required volume of water. Its bowel cleansing action is quite superior to the current bowel cleansing products on the market, even in constipated or bloated patients. In alternative embodiments, these components are used in doses (e.g., unit dosages) of between 1 mg and 30 grams or more, or at a dosage of about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 grams or more, within a composition of the invention, e.g., a liquid (e.g., formulated as a drink, a soup or a soup-like composition), a suspension, a gel, a geltab, a semisolid, a tablet, or sachet, a lozenge or a capsule. In alternative embodiments, these components are used in doses (e.g., unit dosages) of between about 10 grams to 40 grams, or between about 20 grams to about 36 grams; or, at about 15, 16, 17, 18, 19, 20, 21, 22, 23, 24, 25, 26, 27, 28, 29, 30, 31, 32, 33, 34, 35, 36, 37, 38, 39 or 40 or more grams.

Exemplary capsules of the invention are in the formulation described in Example 1, below. In alternative embodiments, the capsules (or other unit dosage formulations, e.g., tablets, sachets, geltabs, lozenges and the like) can be administered in a dosage (e.g., a unit dosage) regimen of from between about 10 capsules and 70 capsules (or other unit dosage formulations), or between about 24 to 36 capsules, at about 30 capsules (or other unit dosage formulations) per patient, or about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 or more capsules (or other unit dosage formulations), or an adjusted number or unit dosages, or total dosages, as required for an individual's (e.g., patients) needs.

For example, in constipated or bloated patients capsule (or other unit dosage formulations) numbers can be increased—and in one embodiment, is done so during the actual preparation by the patient, so incorporating a 'graded-dosage' concept. In those patients with soft, frequent motions they can decrease the number. The type of fluids ingested by the patient with the capsules can be at the patients discretion (e.g., tea, Diet Coke, water, sugar-free juices or drinks) provided that no sugars or potentially volatile agents are present. This greatly improves the palatability of the bowel preparation process and hence compliance. Ideally it requires no more than about 2 liters (liters) of fluids to be taken by the patient and the composition achieves very satisfactory cleansing with watery stools and a clean caecum.

In one embodiment, the invention provides a dry composition to be encapsulated (or otherwise manufactured in a comparable unit dosage formulations, e.g., a geltab) in between 10 and 70 capsules (or other unit dosage formulations) and to be ingested by individuals (e.g. patients) in various timing formats. If can be ingested as between about 2 to 10, or between about 6 to 8 capsules (or other unit dosage formulations) every hour, or about 1, 2, 3, 4, 5, 6, 7, 8, 9, 10, 11, 12, 13, 14, 15, 16, 17, 18, 19, 20 capsules (or other unit dosage formulations) or more per hour, in conjunction with oral fluids of the patient's choice and can be used for colonoscopic preparation or preparation for surgery or other procedures.

In alternative embodiments, the invention provides a cleansing solution for the colon for patients with constipation or bloating as a disorder to be treated long term. The individual (e.g., a patient) can ingest between 5 and 15 capsules (or other unit dosage formulations) per day to help regular bowel actions occurring. This treatment can be taken long-term basis with safety.

Erythritol

In alternative embodiments, the invention provides compositions comprising an erythritol, or (2R,3S)-butane-1,2,3,4-tetraol, or equivalent isomers or sugar substitute isoforms. The erythritol component can make a contribution at several levels in this preparation. For example, while the invention is not limited by any particular mechanism of action, erythritol can promote the absorption of electrolytes in the small bowel which other bowel lavages generally deplete in patients. This is achieved through proximal small bowel passive diffusion utilizing non-saturable kinetics, thus providing a distinct advantage in better re-absorption of not only the polyol erythritol but also co-transporting electrolytes, notably sodium and potassium; see e.g., Ross (1972) J. of Clin. Invest. 51:2414; Bernt (1996) Reg. Toxicol. and Pharmacol. 24:S191-S197. In alternative embodiments, when the composition contains additional potassium, sodium and magnesium, these electrolytes are preferentially reabsorbed in the small bowel through the action of erythritol. Thus, one of the major problems with bowel preparations can be minimized since patients have fewer episodes relating to dehydration, including headaches and lightheadedness. There also can be a reduction in nausea and vomiting otherwise experienced by patients taking many current bowel preparations and hence this preparation is much more acceptable to patients.

Secondly, while the invention is not limited by any particular mechanism of action, erythritol can maintain renal homeostasis by being excreted predominantly in the kidneys without promoting an osmotic diuresis, and thus doss not lead to dehydration of the patient. Indeed, Erythritol is associated with a higher urine osmolality and does not influence creatinine, citrate, urea or electrolytes including sodium, potassium, chloride and phosphate; see e.g., Tetzloff (1996) Reg. Toxicol. & Pharmacol 24:S286-S295; Bornet (1996) Reg. Toxicol. & Pharmacol. 24:S296-S302; Node (1992) J. Nutri 122:1266-1272. Such conservation of the electrolytes and body water with normal serum osmolarity can reduce the risk of hypotension, hyponatremia, nausea and vomiting that is seen commonly with other preparations currently on the market; see e.g., Bornet (1996) supra. The reduction in hyponatraemia also can reduce the risk of more serious side effects of other preparations including convulsions and acute renal failure relating to phosphate toxicity.

Thirdly, while the invention is not limited by any particular mechanism of action, erythritol can be metabolically inert in an individual or patient with a low caloric value and having no effect on blood sugar. All of the safety studies of erythritol show no toxicological effects, and erythritol does not have any carcinogenic, mutagenic or teratogenic potential; see e.g., Munro (1998) Food Chem. Toxicol. 36:1139-1174.

Fourthly, while the invention is not limited by any particular mechanism of action, erythritol—unlike degradable and minimally-degradable sugars such as mannitol—is resistant to metabolism by bowel bacteria, with recent studies showing no significant metabolism by faecal (fecal) flora; see e.g., Hiele (1993) Br. J. Nutr. 69:169-176; Arrigoni (2005) Br. J Nutr 94:643-646. Hence, in one alternative embodiment (or use), there is no explosive potential in patients during colonoscopy and polypectomy using electrocautery. Erythritol can be completely resistant to bacterial attack unlike the more easily fermentable substrates. Furthermore, while the invention is not limited by any particular mechanism of action, only about 10% of the ingested erythritol in this exemplary preparation actually enters the colon; see e.g., Arrigoni (2005) Br. J. Nutr. 94:643-646. In alternative embodiments, individuals (e.g., patients) are administered between about 1 to about 40 grams, or between about 8 to 15 grams, of erythritol (or equivalent isomers or sugar substitute or synthetic isoforms) per day; or, about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 or more grams, of erythritol (or equivalent isomers or sugar substitute or synthetic isoforms) are administered per day.

Erythritol can be produced, e.g., by any method known in the art, e.g., as described in U.S. Pat. Nos. 6,074,857; 6,001,616; 5,962,287; 5,981,241; 6,902,739.

In some embodiments, the composition includes sugar or polyol substitute isoforms. Suitable sugars include minimally degradable sugars (for example sugars having a carbohydrate moiety that is substantially resistant to endogenous digestion in the gastrointestinal tract) and degradable sugars. Suitable sugars and polyol substitute isoforms include xylose, xylotriose, oligosaccharides such as xylooligosaccharides, fructooligosaccharides, fructosans, galactooligosaccharides, mannitol, glucose, L-glucose, sucrose, fructose, galactose, lactose or lactulose. Suitable polyol substitute isoforms include glycol, glycerol, threitol, arabitol, xylitol, ribitol, mannitol, sorbitol, dulcitol, iditol, isomalt, maltitol, lactitol and polyglycitol.

Bisacodyl

In alternative embodiments, the invention provides compositions comprising a bisacodyl, or pyridin-2-ylmethanediyl)dibenzene-4,1-diyl diacetate, or 4,4'-(pyridin-2-ylmethylene)bis(4,1-phenylene) diacetate, or a bioequivalent diphenylmethane. In alternative embodiments, the bisacodyl or bioequivalent diphenylmethane is formulated at or less than about 25 mg, 24 mg, 23 mg, 22 mg, 21 rag, 20 mg, 19 mg, 18 mg, 17 mg, 16 mg, 15 mg, 14 mg, 13 mg, 12 mg, 11 mg, 10 mg, 9 mg, 8 mg, 7 mg, 6 mg, 5 mg, 4 mg, 3 mg, 2 mg or 1 mg or less, or are between about 1 and 25 mg per dosage.

In alternative embodiments, a formulation or composition of the invention comprises between about 10 mg to about 1, 2, 3, 4 or 5 or more grams (g) bisacodyl, or between about 75, 80, 85, 90 or 100 mg to about 150 to 200 mg (e.g., for a normal patient) bisacodyl, or between about 100, 110, 120, 130, 140 or 150 mg to about 1, 2, 3, 4 or 4.5 g or more bisacodyl for a constipated patient In one embodiment, a bisacodyl or a bioequivalent diphenylmethane is used in a preparation of the invention at a final dose of about 10 mg spread over the entire course of the ingestion; this can reduce any peak dosage levels at which side effects occur and exposes the gut to much lower concentrations of bisacodyl than is currently available to patients for colonoscopy preparation or for constipation or bloating treatment. Hence the potential for cramping or adverse effects is minimized with this formulation.

In alternative embodiments, the bisacodyl is DULCO-LAX™, DUROLAX™, FLEET™, ALOPHEN™ or CORRECTOL™.

Bisoxatin

In alternative embodiments, the invention provides compositions comprising a bisoxatin (or 2,2-bis(4-hydroxyphenyl-2H-benzo[b][1,4]oxazin-3(4H)-one), or bisoxatin acetate, or equivalent. In alternative embodiments, a formulation or composition of the invention comprises between about 10 mg to about 1, 2, 3, 4 or 5 or more grams (g) bisacodyl, or between about 75, 80, 85, 90 or 100 mg to about 150 to 200 mg (e.g., for a normal patient) bisacodyl, or between about 100, 110, 120, 130, 140 or 150 mg to about 1, 2, 3, 4 or 4.5 g or more bisacodyl for a constipated patient In alternative embodiments, the bisoxatin is LAXONALIN™, MARATAN™, TALSIS™, TASIS™.

Additional Optional Ingredients

In alternative embodiments, hexaminolevulinate, or CYSVIEW™, or hexaminolevulinate HCl, is added to a composition of the invention, e.g., a capsule or tablet, which can be ingested late in the preparation or dosage regimen. The amount that is required can be between about 5 mg and 500 gm, or about 100 g. Due to a large quantity of hexaminolevulinate passing in the colon, a larger volume can therefore be included to increase attachment to polyps. In some embodiments, only a small volume of hexaminolevulinate is required, and it will take up no greater volume than about 2 of the 900 mg capsules (e.g., 1.8 gm).

In alternative embodiments, simethicone (or any mixture of polydimethylsiloxane and silica gel) or similar surfactant is added into a composition of the invention; optionally between about 5 mg and 450 mg can be added. In specific embodiments, 100 mg of simethicone is added to the composition. The addition of lubricants such as glycerol or silicone to the formulation can also help with colonoscope insertion and facilitation within the performance of the colonoscopy.

Unit Dosage Forms and Formulations and Delivery Vehicles

In alternative embodiments, a composition is manufactured, labeled or formulated as a liquid, a suspension, a spray, a gel, a geltab, a semisolid, a tablet, or sachet, a capsule, a lozenge, a chewable or suckable unit dosage form, or any pharmaceutically acceptable formulation or preparation. In alternative embodiments, a composition of the invention is incorporated into a food, a feed, a drink, a nutritional or a food or feed supplement (e.g., liquid, semisolid or solid), and the like.

For example, a composition of the invention can be manufactured, labeled or formulated as an orally disintegrating tablet as described e.g., in U.S. Pat. App. Publication No. 20100297031. A composition of the invention can be a polyol/thickened oil suspension as described in U.S. Pat. Nos. 6,979,674; 6,245,740. A composition of the invention can be encapsulated, e.g., encapsulated in a glassy matrix as described e.g., in U.S. Pat. App. Publication No. 20100289164; and U.S. Pat. No. 7,799,341. A composition of the invention can be manufactured, labeled of formulated as an excipient particle, e.g., comprising a cellulosic material such as microcrystalline cellulose in intimate association with silicon dioxide, a disintegrant and a polyol, sugar or a polyol/sugar blend as described e.g., in U.S. Pat. App. Publication No. 20100285164. A composition of the invention can be manufactured, labeled or formulated as an orally disintegrating tablet as described e.g., in U.S. Pat. App. Publication No. 20100278930. A composition of the invention can be manufactured, labeled or formulated as a spherical particle, as described e.g., in U.S. Pat. App. Publication No. 20100247665, e.g., comprising a crystalline cellulose and/or powdered cellulose. A composition of the invention can be manufactured, labeled or formulated as a rapidly disintegrating solid preparation useful e.g. as an orally-disintegrating solid preparation, as described e.g., in U.S. Pat. App. Publication No. 20100233278. A composition of the invention can be manufactured, labeled or formulated as a solid preparation for oral application comprising a gum tragacanth and a polyphosphoric acid or salt thereof, as described e.g., in U.S. Pat. App. Publication No. 20100226866. A composition of the invention can be manufactured, labeled or formulated using a water soluble polyhydroxy compound, hydroxy carboxylic acid and/or polyhydroxy carboxylic acid, as described e.g., in U.S. Pat. App. Publication No. 20100222311. A composition of the invention can be manufactured, labeled or formulated as a lozenge, or a chewable and suckable tablet or other unit dosage form, as described e.g., in U.S. Pat. App. Publication No. 20100184785. A composition of the invention can be manufactured, labeled or formulated in the form of an agglomerate, as described e.g., in U.S. Pat. App. Publication No. 20100178349. A composition of the invention can be manufactured, labeled or formulated in the form of a gel or paste, as described e.g., in U.S. Pat. App. Publication No. 20060275223. A composition of the invention can be manufactured, labeled or formulated in the form of a soft capsule, as described e.g., in U.S. Pat. No. 7,846,475, or U.S. Pat. No. 7,763,276.

In one embodiment, a composition of the invention is incorporated into a food, a feed, a drink, a nutritional or a food or feed supplement (e.g., liquid, semisolid or solid), and the like, as described e.g., in U.S. Pat. App. Publication No. 20100178413. In one embodiment, a composition of the invention is incorporated into (manufactured as) a beverage as described e.g., in U.S. Pat. No. 7,815,956. For example, a composition of the invention is incorporated into a yogurt, an ice cream, a milk or milkshake, a "frosty", "snow-cone", or other ice-based mix, and the like.

The polyols used in compositions of the invention can be micronized polyols, e.g., micronized polyols, e.g., as described e.g., in U.S. Pat. App. Publication No.

20100255307, e.g., having a particle size distribution ($d_{50}$) of from 20 to 60 μm, and a flowability below or equal to 5 s/100 g, or below 5 s/100 g.

The invention will be further described with reference to the following examples; however, it is to be understood that the invention is not limited to such examples.

EXAMPLES

Example 1: Exemplary Formulations of the Invention

Exemplary formulation 1 comprises:

| | |
|---|---|
| Bisacodyl or Bisoxatin | 10 mg, |
| Magnesium sulphate | 10.24 gm, |
| Sodium Sulphate | 5.76 gm, |
| Potassium Gluconate | 4.4 gm, |
| Erythritol | 10.24 gm. |

In alternative embodiments, for formulation 1, and other formulations of the invention, capsules and other unit dosage forms and formulations are formulated as described herein.

For example, in one embodiment, for diarrhea, capsules (or tablets, etc) at a dosage schedule of four capsules every 20 minutes are administered (e.g., self-administered by patient); in one embodiment, between about 25 and about 35 total capsules (or tablets, etc.) are administered (e.g., self-administered by patient).

In one embodiment, for use in colonoscopy preparation, twenty-four (24) capsules are taken at intervals of between about 5 to 15 tablets capsules (or tablets, etc.) with approximately liquid (e.g., two glasses of water or equivalent) per hour.

In one embodiment, for use in capsule endoscopy (e.g., for anaemia (anemia) investigation) preparation, between about 15 to about 35 capsules of the capsules (or tablets, etc.) are administered, e.g., self-administered; where in one embodiment, about 5 capsules (or tablets, etc.) are taken, or about 1, 2, 3, 4, 5, 6, 7, 8, 9 or 10 or more capsules (or tablets, etc.) are taken, about every half an hour, or at about every 15 to 45 minutes, is taken until patient develops diarrhea.

In one embodiment, for use in virtual colography preparation, patient is administered, e.g., self-administered, about 8 capsules (or tablets, etc.) about every hour (or about 1, 2, 3, 4, 5, 6, 7, 8, 9, 10, 11 or 12 or more capsules (or tablets, etc.) are taken about every hour) with about 2 liters of water or other fluids (or mixtures thereof). Diarrhoea (diarrhea) is expected to begin around the second hour; then will become quite watery; the virtual colography can be carried out the following day.

Exemplary formulation 2 comprises:

| | |
|---|---|
| 10.0 mg | Bisacodyl or Bisoxatin |
| 10.24 gm | Magnesium Sulphate |
| 5.76 gm | Sodium Sulphate |
| 4.48 gm | Potassium Gluconate |
| 4.48 gm | Sodium Chloride |
| 10.24 gm | Erythritol |

Seven (7) patients have undergone bowel preparation using exemplary formulation 2; results from evaluations: 2 have had excellent scores, 2 have had good scores and 3 received fair scores, one of which had an obstructing rectal cancer and the other had a history of severe constipation.

From a side effect point of view, the feedback has been reassuring, i.e., few side or not severe side effects were reported. All patients, especially those which have used previous bowel preparation products, agree that the capsules are much more pleasant to take (even if they are substantial in size): they experienced no adverse effects, apart from the expected mild abdominal pain, 2 our of 7 experienced mild to severe headaches and attribute it to lack of food rather than as a result of the capsules themselves. Most patients also agree that the method was easy to follow and worthwhile.

Overall, the capsules have been a success in eliminating unnecessary and unpleasant side effects which would usually cause patients to postpone their procedures for as long as possible. This has a significant impact on the patient's well being as, polyps and other potential threats, can be located and removed before they become life threatening.

They have also been successful in reducing the "grouse" (complaining) factor. The fact that (in one embodiment) the preparation comes in a capsulated form, draws the attention of patients with previous ill experiences with the sachet forms of the preparation. Since all agree that they prefer the capsules and would use them again, the capsules nave been successful in this matter as well.

Currently, these erythritol bowel preparation formulations of the invention (e.g., as capsules) have shown adequate bowel clean out, with little to no side effects, and patients expressed a willingness to take this form of this exemplary preparation again.

Further exemplary Formulations comprise (all formulations of the invention optionally can be formulated as a food or a beverage supplement, a dietary supplement, a liquid, an emulsion, a solution, a pill, a tablet, a capsule, a powder or an equivalent):

Exemplary formulation 3 comprises:

| | |
|---|---|
| 10 mg | Bisacodyl or Bisoxatin |
| 7.0 g | magnesium sulphate |
| 15.0 g | sodium sulphate |
| 3.0 g | Potassium gluconate |
| 3.0 g | sodium chloride |
| 3.0 g | Erythritol |

Exemplary formulation 4 comprises:

| | |
|---|---|
| 10 mg | Bisacodyl or Bisoxatin |
| 7 g | magnesium sulphate |
| 6 g | sodium sulphate |
| 3.0 g | Potassium gluconate |
| 3.0 g | sodium chloride |
| 6 g | Erythritol |

Exemplary formulation 5 comprises (using extra $MgSO_4$):

| | |
|---|---|
| 10.0 mg | Bisacodyl or Bisoxatin |
| 13.24 gm | Magnesium Sulphate |
| 5.76 gm | Sodium Sulphate |
| 4.48 gm | Potassium Gluconate |
| 4.48 gm | Sodium Chloride |
| 7.24 gm | Erythritol |

Exemplary formulation 6 comprises:

| | |
|---|---|
| 10.0 mg | Bisacodyl or Bisoxatin |
| 10.24 gm | Magnesium Sulphate |
| 5.76 gm | Sodium Sulphate |
| 4.48 gm | Potassium Gluconate |
| 4.48 gm | Sodium Chloride |
| 10.24 gm | Erythritol |

Exemplary formulation 7 comprises:

| | |
|---|---|
| Bisacodyl or Bisoxatin | 10 mg |
| Mg Sulphate | 7 g |
| Sodium sulphate | 15 g |
| Potassium gluconate | 3 g |
| Sodium chloride | 3 g |
| Erythritol | 3 g |

Exemplary formulation 8 comprises:

| | 1 capsule | 32 capsules | 40 capsules |
|---|---|---|---|
| Sodium picosulphate | 0.625 mg | 20 mg | 25 mg |
| Magnesium sulphate | 156 mg | 5 g | 6.24 g |
| Sodium sulphate | 93.75 mg | 3 g | 3.75 g |
| Potassium gluconate | 62.5 mg | 2 g | 2.5 g |
| Mannitol | 312.5 mg | 10 g | 12.5 g |
| Sodium chloride | 93.75 mg | 2 g | 2.5 g |
| Total | 688.125 mg | 22.02 g | 27.525 g |

Exemplary formulation 9 comprises:

| | 1 capsule | 25 capsules | 28 capsules |
|---|---|---|---|
| Sodium picosulphate | 1.2 mg | 30 mg | 33.6 mg |
| Magnesium sulphate | 320 mg | 8 g | 8.96 g |
| Sodium sulphate | 180 mg | 4.5 g | 5.04 g |
| Potassium gluconate | 140 mg | 3.5 g | 3.92 g |
| Mannitol | 320 mg | 8 g | 8.96 g |
| Sodium chloride | 140 mg | 3.5 g | 3.92 g |
| Total | 1.10 g | 27.53 g | 30.83 g |

Exemplary formulation 10 comprises:

| | 1 capsule | 24 capsules | 32 capsules |
|---|---|---|---|
| Sodium picosulphate | 1.2 mg | 28.8 mg | 38.4 mg |
| Magnesium sulphate | 320 mg | 7.68 g | 10.24 g |
| Sodium sulphate | 180 mg | 4.32 g | 5.76 g |
| Potassium gluconate | 140 mg | 3.36 g | 4.48 g |
| Mannitol | 820 mg | 7.68 g | 10.24 g |
| Sodium chloride | 140 mg | 3.36 g | 4.48 g |
| Total | 1.10 g | 26.43 g | 35.24 g |

In alternative embodiments, the invention provides a combination of exemplary formulations that are designed to be taken in sequence as part of a treatment or colonoscopy preparation regimen. For example, one embodiment would have the patient taking the contents of a first container (e.g., a bottle, blister pack, and the like) before the contents of a second container. In one embodiment, contents of a first container would comprise or consist of capsules (or pills, tablets, geltabs, and the like) comprising the following exemplary formulation: Bisacodyl Magnesium sulphate, Sodium sulphate, Potassium gluconate, Sodium chloride and Erythritol, e.g., in the following exemplary amounts:

Exemplary formulation 11 comprises:

| First bottle (e.g., having about 16 caps) | |
|---|---|
| Bisacodyl or Bisoxatin | 10 mg |
| Magnesium sulphate | 2.95 g |
| Sodium sulphate | 6.32 g |
| Potassium gluconate | 1.26 g |
| Sodium chloride | 1.26 g |
| Erythritol | 1.26 g |

In one embodiment, these capsules could be a different color and/or shape than the capsules (or pills, tablets, geltabs, and the like) in the second formulation (contained in the second container). In one embodiment, the first container (e.g., a bottle) would have between about 10 to 40 or more capsules, e.g., 10, 11, 12, 13, 14, 15, 16, 17, 18, 19, 20, 21, 22, 23, 24, 25, 26, 27, 28, 29, 30, 31, 32 or more capsules. In one embodiment, the second container would have between about 2 to 30 or more capsules, e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or more capsules.

In one embodiment, the second container (e.g., a bottle) would comprise or consist of capsules (or pills, tablets, geltabs, and the like) comprising the following exemplary formulation: Magnesium sulphate, Sodium sulphate, Potassium gluconate, Sodium chloride and Erythritol, e.g., in the following exemplary amounts:

Exemplary formulation 12 comprises:

| Second Bottle (e.g., having about 22 caps) | |
|---|---|
| Magnesium sulphate | 4.05 g |
| Sodium sulphate | 8.68 g |
| Potassium gluconate | 1.74 g |
| Sodium chloride | 1.74 g |
| Erythritol | 1.74 g |

In one embodiment, the invention provides methods for administering a combination of exemplary formulations that are designed to be taken in sequence (a so-called "split protocol") as part of a treatment or a colonoscopy preparation regimen, comprising administering (or instructing to the patient to self-administer) the contents of the first container, then several hours later (e.g., between about 6 to 24 hours later) or the next day (e.g., the morning of the procedure, e.g., a colonoscopy) the contents of the second container.

In alternative embodiments, the first container (e.g., a bottle) comprises capsules (or pills, tablets, geltabs, and the like) having exemplary formulation 11, and the second container (e.g., a bottle) comprises capsules (or pills, tablets, geltabs, and the like) having exemplary formulation 12, and the first container has about 16 capsules to be taken or administered first, and the second container has about 22 capsules to be taken later, e.g., several hours later (e.g., between about 6 to 24 hours later) or the next day (e.g., the morning of the procedure, e.g., a colonoscopy).

In another embodiment, the first container comprises capsules (or pills, tablets, geltabs, and the like) having exemplary formulation 11, and the second container comprises capsules (or pills, tablets, geltabs, and the like) having exemplary formulation 12, and the first container has about 32 capsules to be taken or administered first, and the second container (e.g., a bottle) has about 6 capsules to be taken later, e.g., several hours later (e.g., between about 6 to 24 hours later) or the next day (e.g., the morning of the procedure, e.g., a colonoscopy).

In another embodiment, the kit comprises a container (e.g., a bottle) comprising or consisting of capsules (or pills, tablets, geltabs, and the like) comprising the following exemplary formulation: Bisoxatin, Magnesium sulphate, Sodium sulphate, Potassium gluconate, Sodium chloride, Erythritol, and Simethicone, e.g., in the following exemplary amounts:

Exemplary formulation 13 comprises (per 24 capsules)

| | |
|---|---|
| Magnesium Sulphate | 7 gm |
| Sodium Sulphate | 3 gm |
| Potassium Gluconate | 3 gm |
| Sodium Chloride | 4 gm |
| Erythritol | 2 gm |
| Bisoxatin | 240 mg |
| Simethicone | 100 mg |

In one embodiment, for use in capsule endoscopy (e.g., for anaemia (anemia) investigation) preparation, comprises between about 15 to about 35 capsules of the capsules (or tablets, etc.) are administered, e.g., self-administered; where in one embodiment, about 5 capsules (or tablets, etc.) are taken, or about 1, 2, 3, 4, 5, 6, 7, 8, 9 or 10 or more capsules (or tablets, etc.) are taken, about every half an hour, or at about every 15 to 45 minutes, is taken until patient develops diarrhea.

Example 2: Clinical Investigation of an Exemplary Formulation of the Invention

The following example demonstrates that the compositions of the invention are effective and well tolerated for use in colonoscopy preparation.

A clinical investigation in a male volunteer comprising of the above composition (the exemplary formula of Example 1) was conducted. A light breakfast in accordance to colonoscopy preparation orders was undertaken prior to the intake of the bowel lavage. Twenty-four (24) capsules of the above formulation were taken at intervals of eight (8) capsules with two glasses of water per hour approximately. First bowel movement were observed approximately 30 minutes after the second dose of eight (8) capsules, and desired stool consistency, defined as clear watery stool with no discernible form was observed approximately two hours after last dose intake. The formulation was tolerated well and no headaches, nausea or other adverse effects ware observed whilst undertaking bowel lavage preparation.

Example 3: Use of an Exemplary Formulation of the Invention to Treat a Non-Specific Abdominal Pain 'Syndrome'

The following example demonstrates that the compositions of the invention are effective for treating or ameliorating non-specific abdominal pain syndrome.

A 32 yr old female patient was admitted with recurrent abdominal pain; but more intense in severity on this occasion to the emergency department. The pain was described as generalized with greater attention on the left iliac fossa but could also pass through to the back and was at times aggravated by eating. Numerous investigates failed to show an organic cause including CT scan MRI, β-HCG and blood tests. She was diagnosed with non-specific abdominal pain (syndrome).

In the absence of other diagnoses, the patient was given treatment to flush out the bowel flora in attempt to reduce the pain. She was given 8 capsules of this invention's exemplary formula comprising erythritol and bisacodyl, the formula of Example 1, and started defecating watery stools within 1 and a half hours. The reduction in pain took about 2-3 hours and by the time she had passed 11 stools the pain was virtually gone. This diagnostic therapy was able to refer her to a gastroenterologist for further investigations.

Example 4: Use of an Exemplary Formulation of the Invention in an Acute Case of Constipation The following example demonstrates that the compositions of the invention are effective for treating or ameliorating acute cases of constipation or bloating.

73 year old otherwise well male patient with recently developed back pain prescribed with codeine related medication presented with acute case of constipation. He was seen by his doctor and given laxatives which did not help him. On examination he had a soft abdomen, rectal exam was normal and abdominal x-ray showed fecal loading in ascending colon with no bowel obstruction.

Patient was treated with bowel preparation composition as listed in Example 1 using 8 capsules every 8 hours. His first stool was delayed four and a half hours but thereafter every 15-20 minutes he started passing stools which ultimately became watery. His symptoms disappeared virtually overnight and he followed up with 8 capsules twice daily of the same product for the next four weeks and was able to defecate with ease.

Example 5: Use of an Exemplary Formulation of the Invention in the Treatment of Traveller's Diarrhea A 34 year old male was given the bowel preparation with 32 capsules but also with rifaximin (e.g., XIFAXAN™) to a total dose of 1 gm spread across the 32 capsules. This was in preparation for an overseas trip to Vietnam. Upon returning from Vietnam he recounted how he developed cramping and diarrhea with severe pains that lasted for a couple of days. Initially reticent about taking the capsules, he finally started taking the capsules at a dosage schedule of four capsules every 20 minutes until he finished. With the starting of the flow of the diarrhea secondary to the capsules he flushed out his bowel, the pain was relieved within 4 to 8 hours completely, and continued on with his trips through Asia without further incidence.

Example 6: Use of an Exemplary Formulation of the Invention in Preparation for Capsule Endoscopy A 72 year old patient underwent Capsule Endoscopy for anaemia investigation. He had previously had normal endoscopy and colonoscopy and a bleeding site was being sought in the small bowel. The patient was given 25 capsules of the composition as listed in Example 1. He took 5 capsules every half an hour until he developed diarrhea.

Capsule endoscopy was successful in allowing the capsule to traverse the entire small bowel whereas in the past the capsules ran out of battery life in the mid small bowel. The patient had had small bowel transit which was slow but when the bowel was prepared the capsule was able to traverse the bowel more rapidly and recorded photographs from the entire small bowel. Hence an example of the usefulness of the bowel prep in achieving complete small bowel examination in patients with otherwise slow small bowel transit.

Example 7: Use of an Exemplary Formulation of the Invention for Virtual Colography A 54 year old patient passed blood rectally. He did not want to undergo colonoscopy and chose to have a virtual colography. He was given the preparation contained in Example 1 taking 8 capsules every hour with 2 liters of water or other fluids. His diarrhoea began around the second hour then became quite watery then he was very well prepared for the virtual colography which was carried out successfully in the radiology department on the following day. No particulate stool matter were present on view during the virtual colography.

Example 8: Use of an Exemplary Formulation of the Invention or Colon Preparation Prior to Colonoscopy The following example demonstrates that the compositions of the invention are effective for colon preparation prior to colonoscopy. This example describes the effective use of picosulphate capsules for colon preparation prior to colonoscopy:

|  | 1 capsule | 32 capsules | 40 capsules |
|---|---|---|---|
| Sodium picosulphate | 0.625 mg | 20 mg | 25 mg |
| Magnesium sulphate | 156 mg | 5 g | 6.24 g |
| Sodium sulphate | 93.75 mg | 3 g | 3.75 g |
| Potassium gluconate | 62.5 mg | 2 g | 2.5 g |
| Mannitol | 312.5 mg | 10 g | 12.5 g |
| Sodium chloride | 93.75 mg | 2 g | 2.5 g |
| Total | 688.125 mg | 22.02 g | 27.525 g |

|  | 1 capsule | 25 capsules | 28 capsules |
|---|---|---|---|
| Sodium picosulphate | 1.2 mg | 30 mg | 33.6 mg |
| Magnesium sulphate | 320 mg | 8 g | 8.96 g |
| Sodium sulphate | 180 mg | 4.5 g | 5.04 g |
| Potassium gluconate | 140 mg | 3.5 g | 3.92 g |
| Mannitol | 320 mg | 8 g | 8.96 g |
| Sodium chloride | 140 mg | 3.5 g | 3.92 g |
| Total | 1.10 g | 27.53 g | 30.83 g |

|  | 1 capsule | 24 capsules | 32 capsules |
|---|---|---|---|
| Sodium picosulphate | 1.2 mg | 28.8 mg | 38.4 mg |
| Magnesium sulphate | 320 mg | 7.68 g | 10.24 g |
| Sodium sulphate | 180 mg | 4.32 g | 5.76 g |
| Potassium gluconate | 140 mg | 3.36 g | 4.48 g |
| Mannitol | 320 mg | 7.68 g | 10.24 g |
| Sodium chloride | 140 mg | 3.36 g | 4.48 g |
| Total | 1.10 g | 26.43 g | 35.24 g |

The study described in this example evaluated the efficacy and safety of picosulphate capsules as a bowel preparation; and assessed the side effects and tolerability of picosulphate capsules as a bowel preparation.

Patients were from a clinic who were scheduled to undergo a colonoscopy. Sample Size: 55 patients correctly followed all preparation procedures to completion. Treatment and dosages "24 capsule" version (noted above) picosulphate capsules administered to 23 patients; and "32 capsule" version (noted above) picosulphate capsules administered to 32 patients.

Efficacy Data: Patient Evaluation Form was assessed for compliance and tolerance using score ratings. Doctor Evaluation Form and Anaesthetist Evaluation Form were used to assess efficiency of colonic cleansing during colonoscopy.

Safety Data: Adverse events (AE) were noted by the patient using the Patient Evaluation Form.

Colonoscopic surveillance was used in this study: It is considered to be the gold standard for assessing colonic mucosa. Early detection and prevention of bowel cancers is dependent wholly on colonoscopies and an adequately prepped bowel. Poorly prepped bowels increase the risk of missed lesions, longer procedure duration and a greater need for repeat colonoscopies.[1]

In alternative embodiments, formulations of this invention combine high efficacy with improved tolerability and palatability, whilst preventing electrolyte disturbances; and these properties can address the problem of bowel preparations having: poor palatability, poor patient tolerability and/or causing severe electrolyte disturbances.

In alternative embodiments, formulations of this invention prepare a colon for colonoscopy by reliably emptying the colon of all (or substantially all) faecal matter with no gross or histological alteration of the colonic mucosa. In alternative embodiments, formulations of this invention are well tolerated by the patient, are palatable, and do not cause any electrolyte shifts.

In alternative embodiments, formulations of this invention, e.g., the picosulphate capsules embodiments of this invention, use (comprise) encapsulated sodium picosulphate together with the minimally degradable sugar mannitol to purge the bowel. While the invention is not limited by any particular mechanism of action, sodium picosulphate can work by stimulating the nerve endings in the intestinal wall, hence promoting colonic motility and inhibiting electrolyte and water reabsorption; and, mannitol can work to purge the bowel osmotically. While the invention is not limited by any particular mechanism of action, water content is increased in the colon by mannitol's ability to attract extracellular fluid efflux through the colon wall and maintain oral fluids in the lumen.[5]

In alternative embodiments, formulations of this invention are encapsulated, and encapsulation of these exemplary formulations can significantly increase preparation palatability. In alternative embodiments, formulations of this invention solve the palatability recurring problem (where bowel preparations either tested too salty or required copious amounts of liquid to be consumed). In alternative embodiments, formulations of this invention, this is overcome by encapsulation of the ingredients; a highly palatable delivery system which may increase patient compliance.

In alternative embodiments, encapsulation of exemplary formulations also helps to maintain efficacy of the bowel preparation, as the sodium picosulphate does not begin working until it has reached the gut. It is mainly absorbed in the small intestine where it is most required for an effective clean out.

In alternative embodiments, electrolytes are included in exemplary preparations to reduce electrolyte loss during bowel purgation and create an iso-osmotic environment, thereby reducing the risk of electrolyte disturbances. In alternative embodiments, various salts are used to decrease the symptoms of dehydration and other side effects, and thus improve tolerability of the bowel preparation.

Method

Participants: 55 patients correctly followed all preparation procedures to completion. All 55 patients were aged between 18 to 70 years old and were scheduled to undergo a colonoscopy at a clinic.

Investigational Procedures: Patients aged 18 to 70 scheduled to undergo a colonoscopy at a clinic were informed of a new investigational alternative to the currently marketed bowel preparations. Fully informed consent was obtained and patients were given either the "24" formulation or the "32" formulation (described above) picosulphate capsules. An administration protocol and a Patient Evaluation Form assessing patient compliance and tolerability were also given to the patient.

Patients then returned to the clinic for their scheduled colonoscopies. Completed Patient Evaluation Forms were collected and a colonoscopy was performed. Doctor and anaesthetist evaluated the efficacy of the picosulphate capsules using the Doctor Evaluation Form and Anaesthetist Evaluation Form; both forms based on the Ottawa Bowel Preparation Scale. Doctor and anaesthetist assessed the cleanliness of five sections of the bowel—the rectum, sigmoid/descending colon, transverse colon, ascending colon/hepatic flexure, and caecum. The volume of fluid in the colon was also assessed.

Evaluation Scoring: The bowel preparation evaluation scoring methods employed were based on the Ottawa Bowel Preparation Scale and used a five point rating system. Five sections of the bowel (rectum, sigmoid/descending colon, transverse colon, ascending colon/hepatic flexure, and caecum) were rated from 0-4 cleanliness (0=Excellent, 1=Good, 2=Fair, 3=Poor, 4=Inadequate) independently by both Doctor and Anesthetist.

The volume of fluid present in the entire colon was also assessed using a three point rating system. Volume of fluid was rated from 0-2 (0=small volume, 1=medium volume, 2=large volume) independently by both doctor and anaesthetist.

Scores rating the cleanliness of each section of the colon and volume of fluid present were then combined for each patient to produce a total score. An average was then obtained from the doctors' and anaesthetists' total scores and general evaluation grade was assigned based on the following grading system:

| Average Total Score | General Evaluation Grade |
|---|---|
| 0-5 | EXCELLENT |
| 6-9 | GOOD |
| 10-13 | FAIR |
| 14-19 | POOR |
| 20-22 | INADEQUATE |

Results:

Patient Evaluation:

All 55 patients were able to complete the picosulphate capsule preparation without difficulty with 43/55 (78.2%) patients and 12/55 (21.8%) patients finding the preparation "easy" and "somewhat easy" to complete, respectively.

54/55 (98.2%) of patients reported that they would prefer to take the picosulphate capsules again for future procedures. Of these patients who stated that they would use picosulphate capsules again 42 (77.8%) have previously taken other bowel preparations.

Patient compliance was also high with all 56 patients correctly following the picosulphate capsule administration protocol.

Doctor and Anaesthetist Evaluation:

47/55 (85.5%) patients who trialed the picosulphate capsules achieved an Excellent/Good general evaluation grade (Average total score of 0-9) for cleanliness of the whole bowel. The average doctor and an anaesthetist scores for rating the cleanliness of the rectum, sigmoid/descending colon, transverse colon, ascending colon/hepatic flexure, and caecum during colonoscopy were 0.69, 0.71, 0.70, 0.91, and 1.17, respectively (0=Excellent, 1=Good). The average doctor and an anaesthetist score for rating the volume of fluid present in the entire colon was 0.57, representing a small to medium volume.

Adverse Events:

No serious adverse events were reported and capsules were well tolerated by patients. Of the adverse events experienced, effects were mild and transient in nature. 22 patients reported a mild headache, 19 patients reported nausea, and 2 patients reported dizziness and vomiting, 8 patients experienced no side effects at all.

DISCUSSION AND CONCLUSION

In overall cleansing of the colon prior to colonoscopy, picosulphate capsules were effective with a majority of patients (85.5%) achieving an Excellent/Good overall evaluation grade. Doctor and anaesthetist scores rating the rectum, sigmoid/descending colon, transverse colon, ascending colon, and caecum did not reflect any significant differences in picosulphate's ability to effectively cleanse different sections of the colon. All sections of the colon scored an average between 0.69 and 1.17 representing an Excellent to Good evaluation score. Volume of fluid present within the entire colon scored an average of 0.57 representing a small to medium volume of fluid present.

Five patients scored a "Fair" evaluation grade, 4 of whom always present with a poorly prepped bowel despite using different preparations, 3 patients scored a "Poor" evaluation grade, 2 of whom had an ongoing history of severe constipation.

All adverse events were mild in nature and transient. All adverse events reported were also expected and are frequently reported after completion of currently marketed bowel preparations.[2] 8/55 (14.5%) patients reported no side effects at all after completion of picosulphate capsules.

Despite adverse events, tolerability and palatability of picosulphate capsules were significantly high in all patients with 100% (55/55) of patients finding the capsules easy or somewhat easy to take and 98.2% (54/55) of patients reporting preference for picosulphate capsules over alternative bowel preparations. This was also reflected in the high patient compliance with all 55 patients correctly and ably following the picosulphate preparation protocol.

In conclusion, these clinical observations demonstrated that picosulphate capsules are an affective, safe and tolerable new bowel preparation alternative for patients.

Example 9: Exemplary Formulation—Clinical Observations

This example provides information and clinical results demonstrating the efficacy of an exemplary formulation 13 of the invention:

| | |
|---|---|
| Bisoxatin | 240 mg |
| Magnesium sulphate | 7 gm |
| Sodium sulphate | 3 gm |
| Potassium gluconate | 3 gm |
| Sodium chloride | 4 gm |
| Erythritol | 2 gm |

32 patients aged between 18 to 70 years scheduled to undergo a colonoscopy underwent the capsule preparation after being informed of a novel bowel preparation (exemplary formulation 13 of this invention) which offered an alternative to currently marketed bowel purgatives. Written informed consent was obtained and patients were given 23 capsule formulation containing 240 mg bisoxatin. Patients ware also given an administration protocol, patient questionnaires and a drinking log to complete. Patients commenced bowel purgatives at 2 pm in the afternoon, and were allowed carbonated beverages that were artificially sweetened in their fluid only diet.

Patients returned to the Clinic for their colonoscopies and completed patient questionnaires were collected. Doctor and anaesthetist evaluated the cleanliness of the bowel independently, once again using the modified Ottawa bowel scale using a five point rating system and evaluating 5 sections of the bowel; rectum, sigmoid/descending colon, transverse colon, ascending/hepatic flexure and caecum.

30/32 patients were given an 'excellent/good' rating and 31/32 of the patients reporting that they would prefer to take the capsules again with 14/31 of those patients reporting having previously taken other bowel purgatives.

No serious adverse events were reported with the most common being nausea and headaches, however these adverse effects were considered transient in nature.

REFERENCES

1. Lai, E J, Calderwood A H, Doros G, Fix O K, Jacobson B C. The Boston bowel preparation scale: a valid and reliable instrument for colonoscopy-oriented research. Gastrointestinal Endoscopy 2009:69(3):620-5.
2. Parente F, Marino B, Crosta C. Bowel preparation before colonoscopy in the era of mass screening for colon-rectal cancer: A practical approach. Digestive and Liver Disease 2009141:87-95.
3. Norgine Pty Ltd. Deaths and kidney failures call bowel preparation safety into question, 2008. United Kingdom.
4. Song S H, Vielle C. Recent advances in the biological production of mannitol. Applied Microbiology and Biotechnology 2009; 84(1):55-62.
5. Winawer S, et al. Colorectal cancer screening and surveillance: clinical guidelines and rationale—updated based on new evidence. Gastroenterology 2003; 12:544-60.

A number of embodiments of the invention have been described. Nevertheless, it will be understood that various modifications may be made without departing from the spirit and scope of the invention. Accordingly, other embodiments are within the scope of the following claims.

The invention claimed is:

1. A composition comprising:
(i) from about 1 to about 25 milligrams (mg) bisoxatin (or 2,2-bis(4-hydroxyphenyl)-2H-benzo[b][1,4]oxazin-3 (4H)-one), or bisoxatin acetate,
(ii) from about 1 to about 25 grams of erythritol, or (2R,3S)-butane-1,2,3,4-tetraol, or isomers, sugar or polyol substitute isoforms, and
(iii) a pharmaceutically acceptable salt or salts, wherein the pharmaceutically acceptable salt or salts comprise from about 1 to about 40 grams of a pharmaceutically acceptable salt or pharmaceutically acceptable salts and comprise at least one sodium salt selected from the group of: a monobasic sodium phosphate, dibasic sodium phosphate, and/or tribasic sodium phosphate, a sodium sulfate, a sodium chloride, a sodium gluconate, a sodium citrate and a sodium aspartate.

2. The composition of claim 1, wherein the composition comprises about 10 milligrams (mg) bisoxatin or (2,2-bis (4-hydroxyphenyl)-2H-benzo[b][1,4]oxazin-3(4H)-one), or bisoxatin acetate.

3. The composition of claim 1, wherein the composition is formulated for use as a purgative, a colonic cleanser, or for orthostatic lavage.

4. The composition of claim 1, wherein the composition comprises from about 8 to about 15 grams of erythritol.

5. The composition of claim 4, wherein the composition comprises about 10.24 grams of erythritol.

6. The composition of claim 4, wherein the composition comprises about 2 grams of erythritol.

7. The composition of claim 4, wherein the composition comprises about 3 grams of erythritol.

8. The composition of claim 4, wherein the composition comprises from about 7.24 grams of erythritol.

9. The composition of claim 1, wherein the composition comprises from about 8 to about 15 grams of the pharmaceutically acceptable salt or salts.

10. The composition of claim 1, wherein the composition comprises from about 15 to about 28 grams of the pharmaceutically acceptable salt or salts.

11. The composition of claim 1, wherein the pharmaceutically acceptable salt or salts further comprises a water-soluble salt.

12. The composition of claim 1, wherein the pharmaceutically acceptable salt or salts further comprises a water-soluble potassium salt.

13. The composition of claim 12, further comprising a sodium salt, wherein the water-soluble potassium salt is in an amount, by weight, of from about 0.05 to about 1 times the weight of a sodium salt in the composition.

14. The composition of claim 1, wherein the pharmaceutically acceptable salt or salts further comprises a water-soluble magnesium salt.

15. The composition of claim 14, further comprising a sodium salt, wherein the weight of magnesium ions of the magnesium salt in the composition is from about 0.1 to about 10 times the weight of sodium ions in the composition.

16. The composition of claim 1, further comprising at least one salt selected from the group consisting of: a calcium salt, a calcium carbonate, a calcium acetate, a citrate salt, a calcium citrate, a magnesium salt, a magnesium sulfate, a magnesium citrate, a magnesium phosphate, a potassium salt, a potassium gluconate, a potassium tartrate, a potassium chloride, an acetate salt, an adipate salt, an alginate salt, an aspartate salt, a benzoate salt, a benzenesulfonate salt, a bisulfate salt, a butyrate salt, a camphorate salt, a camphor sulfonate salt, a digluconate salt, a glycerophosphate salt, a hemisulfate salt, a heptanoate salt, a hexanoate salt, a fumarate salt, a hydrochloride salt, a hydrobromide salt, a hydroiodide salt, a 2-hydroxyethansulfonate (isothionate) salt, a lactate salt, a maleate salt, a methane sulfonate salt, a nicotinate salt, a 2-naphthalene sulfonate salt, an oxalate salt, a palmitoate salt, a pectinate salt, a persulfate salt, a 3-phenylpropionate salt, a picrate salt, a pivalate salt, a propionate salt, a succinate salt, a tartrate salt, a thiocyanate salt, a phosphate salt, a glutamate salt, a bicarbonate salt, a p-toluenesulfonate salt, a undecanoate salt, or any equivalent salt, or any mixture thereof.

17. The composition of claim 1, wherein the composition further comprises one or more of a defoaming agent, a surfactant agent, a lubricant, an acid neutralizer, a marker, a cell marker, a drug, an antibiotic and/or a contrast agent.

18. The composition of claim 17, wherein the marker comprises (i) a hexaminolevulinate, an indigo carmine or a methylene blue or an equivalent cell marker, or (ii) an antibody specific for a normal or abnormal cell phenotype or genotype, or a cancer cell or a polyp.

19. The composition of claim 17, wherein the surfactant agent comprises a simethicone or any mixture of polydimethylsiloxane and silica gel, or equivalent.

20. The composition of claim 19, wherein the surfactant agent comprises simethicone in an amount of from about 5 to 450 mg.

21. The composition of claim 20, wherein the composition comprises simethicone in an amount of about 100 mg.

22. The composition of claim 17, wherein the lubricant is selected from one or more of a magnesium stearate, a hyaluronic acid, a glycerol and/or a silicone.

23. A pharmaceutical composition comprising: the composition of claim 1.

24. The pharmaceutical composition of claim 23, wherein the composition is formulated as a liquid, a suspension, a gel, a semisolid, or as an enteral formulation.

25. The pharmaceutical composition of claim 23, wherein the composition is formulated as a plurality of dosage units, wherein the dosage unit is selected from the group consisting of: a pill, a tablet, a geltab, a lozenge, a sachet and a capsule.

26. The pharmaceutical composition of claim 25, wherein the composition is administered as about 10 to 70 dosage units.

27. The pharmaceutical composition of claim 23, wherein the composition is manufactured with an encapsulating material, wherein optionally the encapsulating material comprises a lubricant.

28. A method of performing a procedure involving the intestine or colon on a subject, comprising administering a first composition comprising the composition of claim 1, optionally wherein the subject is a human or an animal.

29. The method of claim 28, wherein the procedure comprises a colonoscopy, an enteroscopy, an endoscopy, a capsule endoscopy, a viewing of the intestinal or colonic mucosa, a surgical procedure involving the intestine or colon, or a radiological procedure involving the intestine or colon to an individual in need thereof.

30. The method of claim 28, wherein the first composition is administered as a plurality of dosage units, wherein the dosage unit is selected from the group of: a pill, a tablet, a geltab, a lozenge, a sachet and a capsule.

31. The method of claim 30, wherein the procedure is a colonoscopy, and the first composition is administered as about 10 to 40 dosage units.

32. The method of claim 31, wherein the first composition is administered in a dosing regimen of from about 1 to 20 dosage units per hour.

33. The method of claim 28, wherein the subject is administered at least a second composition.

34. The method of claim 33, wherein the at least second composition is administered about 6 to 24 hours after administration of the first composition.

35. The method of claim 33, wherein the at least second composition is administered as a plurality of dosage units comprising about 2 to 32 dosage units.

36. The method of claim 30, wherein the procedure is a capsule endoscopy, and the first composition is administered in a dosing regimen of from 1 to 10 dosage units per half-hour.

37. A method for the amelioration, treatment and/or prevention of constipation or bloating in a subject, comprising administering the composition of claim 1 to the subject in need thereof.

38. The method of claim 37, wherein the composition is administered as a plurality of dosage units, wherein the dosage unit is selected from the group consisting of: a pill, a tablet, a geltab, a lozenge, a sachet and a capsule.

39. The method of claim 38, wherein the composition is administered in a dosing regimen of from about 5 to 15 dosage units per day.

40. The method of claim 37, wherein the constipation or bloating is due to at least one of: travel; change in daily routine; lack of exercise; immobility caused by injury, illness, or aging; dehydration; irritable bowel syndrome; pregnancy; diabetes; hypothyroidism; hypercalcemia; cancer of the colon or rectum; uterine prolapse; vaginal vault prolapse; rectal prolapse; scarring from surgery; injury of the colon or rectum; Parkinson's disease; multiple sclerosis; stroke; hemorrhoids or anal fissures; delaying bowel movements; anxiety; depression; eating disorders; and/or obsessive-compulsive disorder, coeliac disease, muscular dystrophy, myotonic dystrophy, nonspecific abdominal pain, or a neurological condition or any cause of constipation.

41. A method for the treatment of abdominal pain in a subject, comprising administering the composition of claim 1 to the subject in need thereof.

42. A method for the amelioration or treatment of a bowel disease in a subject, comprising administering a composition of claim 1 to the subject in need thereof.

43. The method of claim 42, wherein the bowel disease or condition having a bowel dysfunction component, comprises: an inflammatory bowel disease (IBD), Crohn's disease, hepatic encephalopathy, enteritis, colitis, irritable bowel syndrome (IBS), fibromyalgia (FM), chronic fatigue syndrome (CFS), depression, attention deficit/hyperactivity disorder (ADHD), multiple sclerosis (MS), systemic lupus erythematosus (SLE), travelers' diarrhea, small intestinal bacterial overgrowth, chronic pancreatitis, or a pancreatic insufficiency.

44. A package or kit comprising: the composition of claim 1 and instructions for its use.

45. The package or kit of claim 44, wherein the composition is contained within a first container, wherein the package or kit further comprises at least a second container comprising the composition of claim 1, and the contents of the two containers are designed to be taken in sequence.

46. The package or kit of claim 45, wherein the first container comprises a bottle, a blister pack, or equivalents thereof and the second container comprises a bottle, a blister pack, or equivalents thereof.

47. The package or kit of claim 45, wherein the compositions of the first and second containers are provided as a plurality of dosage units, wherein the dosage unit is selected from the group consisting of: a pill, a tablet, a geltab and a capsule.

48. The package or kit of claim 47, wherein the first container comprises from about 10 to 40 dosage units.

49. The package or kit of claim 47, wherein the second container comprises from about 2 to 32 dosage units.

50. The package or kit of claim 45, wherein the composition of the first container and the composition of the second container are administered from 6 to 24 hours apart.

51. The package or kit of claim 45, wherein the composition of the second container is administered the next day relative to the composition of the first container.

* * * * *